United States Patent
Hernandez

(10) Patent No.: US 11,452,817 B2
(45) Date of Patent: Sep. 27, 2022

(54) SYSTEM FOR DELIVERING MEDICATION

(71) Applicant: Certa Dose, Inc., Denver, CO (US)

(72) Inventor: Caleb Hernandez, Arvada, CO (US)

(73) Assignee: CD ACQUISITIONS, LLC, Denver, CO (US)

( * ) Notice: Subject to any disclaimer, the term of this patent is extended or adjusted under 35 U.S.C. 154(b) by 802 days.

(21) Appl. No.: 14/392,087

(22) PCT Filed: Jan. 30, 2013

(86) PCT No.: PCT/US2013/023873
§ 371 (c)(1),
(2) Date: Sep. 2, 2015

(87) PCT Pub. No.: WO2013/116353
PCT Pub. Date: Aug. 8, 2013

(65) Prior Publication Data
US 2016/0022912 A1 Jan. 28, 2016

Related U.S. Application Data

(60) Provisional application No. 61/717,474, filed on Oct. 23, 2012, provisional application No. 61/593,674, filed on Feb. 1, 2012.

(51) Int. Cl.
*A61M 5/31* (2006.01)
*A61M 5/14* (2006.01)
(Continued)

(52) U.S. Cl.
CPC ............ *A61M 5/3129* (2013.01); *A61M 5/14* (2013.01); *A61M 5/178* (2013.01); *G01F 17/00* (2013.01);
(Continued)

(58) Field of Classification Search
CPC .. A61M 2005/3125; A61M 2005/3126; A61M 2205/3379; A61M 2205/584;
(Continued)

(56) References Cited

U.S. PATENT DOCUMENTS

D280,734 S    9/1985  Bateman
4,713,888 A  12/1987  Broselow
(Continued)

FOREIGN PATENT DOCUMENTS

EP    0983761       3/2000
EP    2548597 A1    1/2013
(Continued)

OTHER PUBLICATIONS

Supplementary European Search Report for European Application No. 13742871.0, dated Jul. 17, 2015, 6 pages.
(Continued)

*Primary Examiner* — Shefali D Patel
(74) *Attorney, Agent, or Firm* — Neugeboren O'Dowd PC

(57) ABSTRACT

Aspects of the present disclosure disclose a system for delivering a medication. In one aspect, the disclosure is directed to a medical dispensing device that includes a label with a series of zones of varying widths, with each of the zones corresponding to a pre-determined volumetric dose of a drug that is correlated to a physical characteristic of a patient. In one specific example, the label is further affixed to the medical dispensing device such that a smallest dose of the drug to be administered corresponds to a first zone that is proximate an opening through which the drug is to be dispensed.

22 Claims, 17 Drawing Sheets

(51) Int. Cl.
*A61M 5/178* (2006.01)
*G01F 17/00* (2006.01)
*A61M 5/315* (2006.01)
*A61M 5/00* (2006.01)

(52) U.S. Cl.
CPC ......... *A61M 5/002* (2013.01); *A61M 5/31525* (2013.01); *A61M 2005/3125* (2013.01); *A61M 2005/3126* (2013.01); *A61M 2205/3327* (2013.01); *A61M 2205/584* (2013.01); *A61M 2205/6009* (2013.01); *A61M 2205/6081* (2013.01); *A61M 2207/00* (2013.01); *A61M 2230/00* (2013.01)

(58) Field of Classification Search
CPC .. A61M 2205/6009; A61M 2205/6081; A61M 2207/00; A61M 2230/00; A61M 2230/005; A61M 2005/3142; A61M 5/14; A61M 5/178; A61M 5/3129; A61M 5/31525; A61M 2205/3327; A61M 2205/50; G01F 17/00
See application file for complete search history.

(56) References Cited

U.S. PATENT DOCUMENTS

| | | | |
|---|---|---|---|
| 4,716,888 A | 1/1988 | Wesner | |
| 4,823,469 A | 4/1989 | Broselow | |
| 4,926,885 A | 5/1990 | Hinkle | |
| 5,010,656 A | 4/1991 | Broselow | |
| 5,016,651 A | 5/1991 | Stalcup et al. | |
| 5,468,224 A | 11/1995 | Souryal | |
| 5,573,529 A | 11/1996 | Haak et al. | |
| 5,692,640 A | 12/1997 | Caulfield et al. | |
| 5,773,258 A | 6/1998 | Birch et al. | |
| 6,132,416 A * | 10/2000 | Broselow | A61J 1/1425 128/898 |
| 6,322,543 B1 | 11/2001 | Singh et al. | |
| 6,338,200 B1 * | 1/2002 | Baxa | A61M 5/31525 222/386 |
| 6,413,241 B1 * | 7/2002 | Slishman | A61J 1/00 604/186 |
| 6,764,469 B2 | 7/2004 | Broselow | |
| D500,342 S | 12/2004 | Stewart et al. | |
| D500,524 S | 1/2005 | Stewart et al. | |
| D547,658 S | 7/2007 | Small et al. | |
| D548,241 S | 8/2007 | Viegers | |
| 7,857,138 B2 | 12/2010 | Temple | |
| 8,062,254 B2 | 11/2011 | MacLean | |
| 8,182,450 B2 | 5/2012 | Moosheimer et al. | |
| 8,361,055 B2 | 1/2013 | Tucker | |
| D684,467 S | 6/2013 | Macaulay et al. | |
| D684,468 S | 6/2013 | Macaulay et al. | |
| D686,492 S | 7/2013 | DiFranza | |
| D687,707 S | 8/2013 | Craig et al. | |
| 8,535,277 B2 | 9/2013 | Oden et al. | |
| 9,019,307 B1 | 4/2015 | Grimm | |
| D741,871 S | 10/2015 | Chung et al. | |
| 9,159,249 B2 | 10/2015 | Ferrara | |
| 9,192,723 B2 | 11/2015 | Creaturo | |
| D745,534 S | 12/2015 | Cho | |
| D747,726 S | 1/2016 | Virk et al. | |
| D748,105 S | 1/2016 | Virk et al. | |
| 9,271,896 B2 | 3/2016 | Clements | |
| 9,272,099 B2 | 3/2016 | Limaye et al. | |
| 9,345,638 B2 | 5/2016 | Ferrara | |
| 9,345,639 B2 | 5/2016 | Ferrara | |
| D771,807 S | 11/2016 | Zalewski | |
| D783,397 S | 4/2017 | Riffe | |
| 9,682,195 B2 | 6/2017 | Tucker | |
| D797,759 S | 9/2017 | Tsujimura et al. | |
| D798,886 S | 10/2017 | Prophete et al. | |
| 9,839,750 B2 | 12/2017 | Limaye et al. | |
| 9,931,469 B2 | 4/2018 | Shain et al. | |
| 9,950,126 B2 | 4/2018 | Basile et al. | |
| D819,060 S | 5/2018 | Friedman et al. | |
| D846,383 S | 4/2019 | Hernandez | |
| 2002/0087121 A1 | 7/2002 | Slishman | |
| 2002/0088131 A1 | 7/2002 | Baxa et al. | |
| 2004/0024368 A1 | 2/2004 | Broselow | |
| 2004/0082855 A1 | 4/2004 | Robar et al. | |
| 2004/0186437 A1 | 9/2004 | Frenette et al. | |
| 2005/0090782 A1 | 4/2005 | Marshall et al. | |
| 2005/0215957 A1 | 9/2005 | Hynes | |
| 2006/0000480 A1 | 1/2006 | Broselow | |
| 2006/0137696 A1 | 6/2006 | Broselow | |
| 2007/0100288 A1 | 5/2007 | Bozeman et al. | |
| 2007/0127623 A1 | 6/2007 | Goldman et al. | |
| 2007/0135772 A1 * | 6/2007 | Grogan, Jr. | A61J 1/00 604/212 |
| 2007/0201614 A1 | 8/2007 | Goldman et al. | |
| 2008/0188814 A1 | 8/2008 | Lavi-Loebl et al. | |
| 2008/0232542 A1 | 9/2008 | Lin | |
| 2009/0126743 A1 | 5/2009 | Wingert | |
| 2009/0149815 A1 | 6/2009 | Kiel et al. | |
| 2010/0056895 A1 | 3/2010 | Temple et al. | |
| 2013/0012886 A1 | 1/2013 | Kawachi | |
| 2013/0101079 A1 | 4/2013 | Hough et al. | |
| 2013/0204225 A1 | 8/2013 | Creaturo | |
| 2015/0057608 A1 | 2/2015 | Hitscherich, Jr. et al. | |
| 2015/0306318 A1 | 10/2015 | Lockhart et al. | |
| 2016/0022920 A1 | 1/2016 | Reeves | |
| 2016/0136050 A1 | 5/2016 | Clements | |
| 2016/0166774 A1 | 6/2016 | Leary | |
| 2016/0166775 A1 | 6/2016 | Oakley et al. | |
| 2016/0250416 A1 | 9/2016 | Hultgren | |
| 2017/0095615 A1 | 4/2017 | Fischer et al. | |
| 2017/0151391 A1 | 6/2017 | Hernandez | |
| 2017/0245811 A1 | 8/2017 | Hernandez | |
| 2017/0304152 A1 | 10/2017 | Hernandez | |
| 2017/0367930 A1 | 12/2017 | Gompf et al. | |
| 2018/0043103 A1 | 2/2018 | Nandigala et al. | |
| 2018/0154088 A1 | 6/2018 | Broselow | |
| 2018/0221581 A1 | 8/2018 | Kumar et al. | |

FOREIGN PATENT DOCUMENTS

| | | |
|---|---|---|
| GB | 2461013 A | 12/2009 |
| JP | 2006507034 A | 3/2006 |
| JP | 2008-171582 A | 7/2008 |
| JP | 2011-143652 A | 7/2011 |
| JP | 2015505510 A | 2/2015 |
| WO | WO 2010/112558 | 10/2010 |
| WO | WO 2011/114917 | 9/2011 |
| WO | WO 2013/116353 | 8/2013 |
| WO | WO 2017/193082 | 11/2017 |
| WO | WO 2017/197145 | 11/2017 |

OTHER PUBLICATIONS

International Search Report and Written Opinion for International Application No. PCT/US2013/023873, dated Jun. 2, 2013, 12 pages.
"Color Coding System Measures Kids' Meds," Healthy Living, KABC-TV/DT, Mar. 24, 2009, 5 pages.
McFadden, M., "New dosing system takes the guesswork out of giving medicine to kids," WNDU—Channel 16, Mar. 12, 2009, 3 pages.
HMC Pharmacy, "New Procedure: Emergency syringes," Harborview Medical Center (Oct. 2010), 1 page.
Frush, K. S. et al., "Evaluation of a Method to Reduce Over-the-Counter Medication Dosing Error," Arch. Pediatr. Adolesc. Med., 158:620-624 (Jul. 2004).
International Search Report and Written Opinion for International Application No. PCT/US2017/031420, dated Aug. 14, 2017, 6 pages.
International Search Report and Written Opinion for International Application No. PCT/US2017/032207, dated Jul. 26, 2017, 9 pages.
Med Alliance Group, Inc., Certa Dose Epinephrine Convenience Kit, Accurate Dosing Confirmed [Online], Retrieved from the

(56) References Cited

OTHER PUBLICATIONS

Internet on Jun. 20, 2018; <URL: https://www.medalliancegroup.com/product/certadose-epinephrine/>, 3 pages.
Excel Spreadsheets Group, 4+ Simple Excel Spreadsheet [Online], Retrieved from the Internet on Feb. 20, 2018; <URL:http://excelspreadsheetsgroup.com/4-simple-excel-spreadsheet/>, 4 pages.
Moreira, M. E. et al., "Color-Coded Prefilled Medication Syringe Decrease Time to Delivery and Dosing Error in Simulated Emergency Department Pediatric Resuscitations," Annals of Emergency Medicine, United States of America, American College of Emergency Physicians, Aug. 2015, vol. 66, No. 2, pp. 97-106.
International Search Report and Written Opinion for International Application No. PCT/US2019/014623, dated Apr. 12, 2019, 12 pages.
Melker, R. et al. "A pediatric gastric tube airway," Critical Care Medicine. 1981. The Williams & Watkins Co.; 9(5):426-427.
Ryu, G. S. et al. "Analysis of liquid medication dose errors made by patients and caregivers using alternative measuring devices", J Manag Care Pharm. Jul.-Aug. 2012;18(6):439-45.
Luten, R. et al. "Managing the unique size-related issues of pediatric resuscitation: reducing cognitive load with resuscitation aids", Acad Emerg Med. Aug. 2002;9(8):840-7.
Moreira, M. E., et al. "Novel, Color-Coded Prefilled Syringe Significantly Decreases Time to Medication Administration, Preparation for Endotracheal Intubation, And Eliminates Critical Dosing Errors in Simulated Pediatric Resuscitations," Circulation. Journal of the American Heart Association. Dec. 4, 2012. 126(23):2798. LBRS-358.
Ito, Kosuke, "Office Action Regarding Japanese Patent Application No. 2018-5557892", dated Mar. 9, 2021, p. 9, Published in: JP.
Decision of Final Rejection received for Japanese Patent Application Serial No. 2018557892 dated Nov. 16, 2021, 9 pages (Including English Translation).

\* cited by examiner

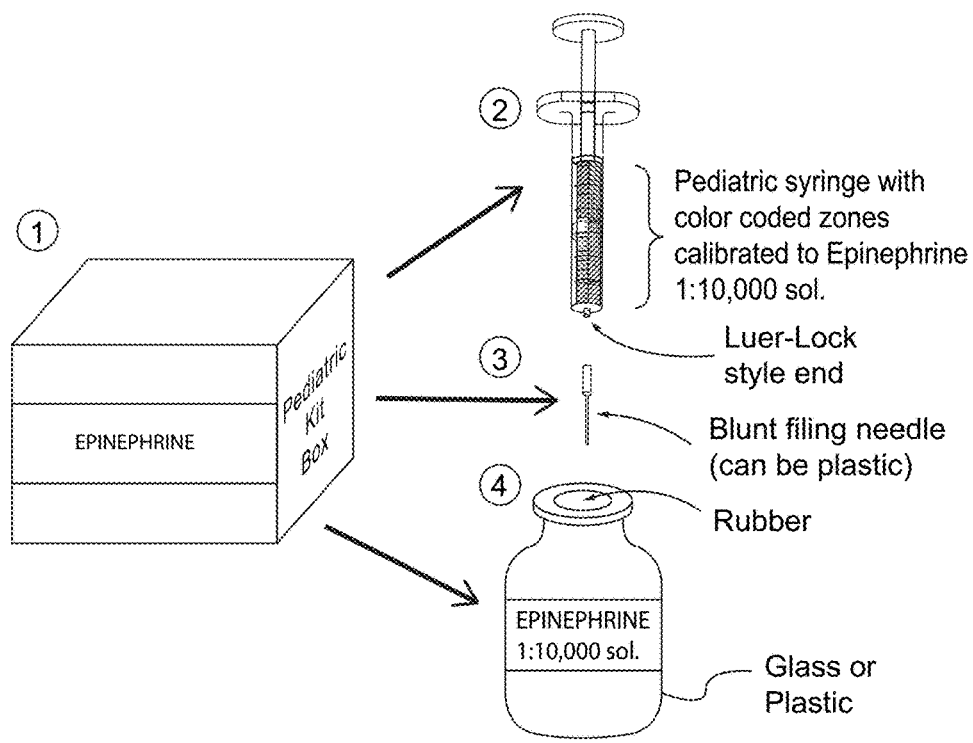
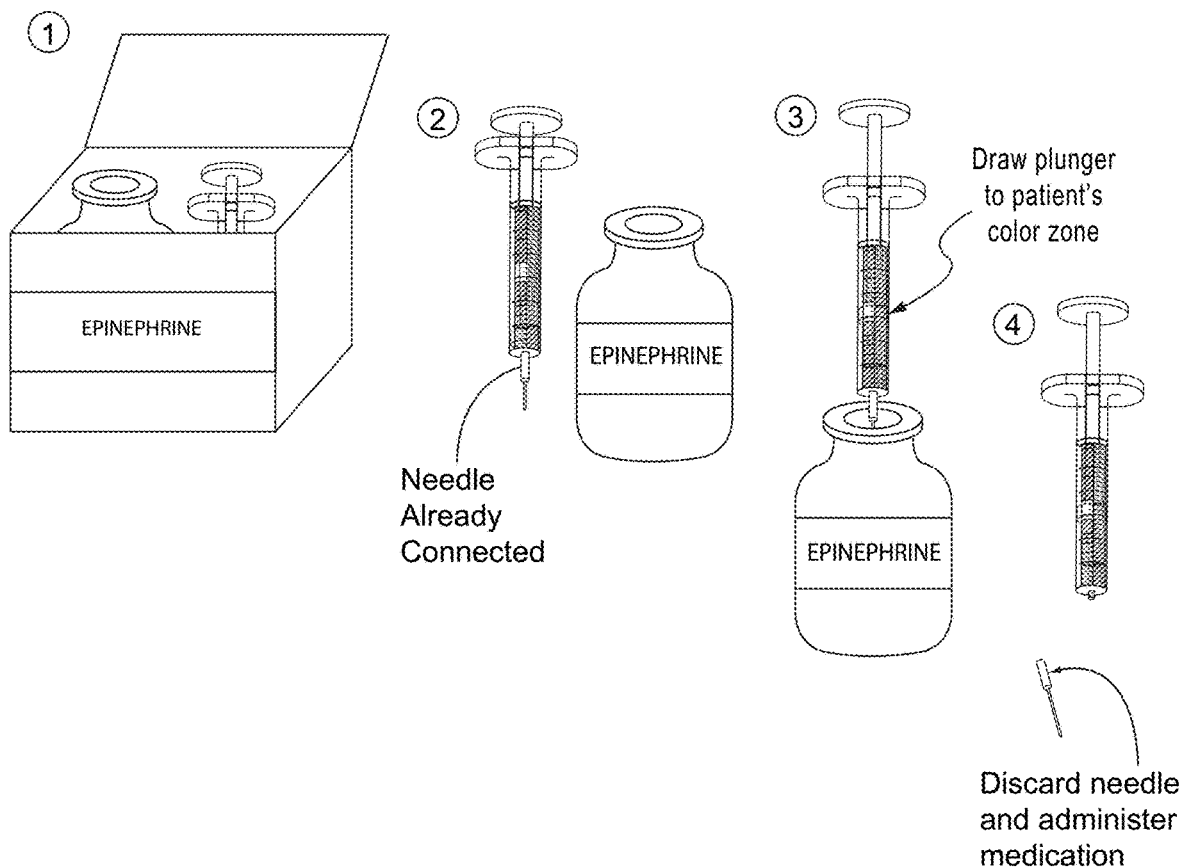
FIG. 7B

SYSTEM FOR DELIVERING MEDICATION

CROSS REFERENCE TO RELATED APPLICATIONS

This is a National Phase application filed under 35 U.S.C. § 371 as a national stage of PCT/US2013/023873, filed Jan. 30, 2013, which claims priority to U.S. provisional application No. 61/593,674 titled "System for Delivering Medication" filed on Feb. 1, 2012 and to U.S. provisional application No. 61/717,474 titled "System for Delivering Medication" filed on Oct. 23, 2012, both of which are hereby incorporated by reference herein.

FIELD OF DISCLOSURE

The present disclosure relates to a medicine-dosing device, and more particularly to a pre-labeled medicine dosing device and method for administering appropriate doses of medicine in an emergency or critical care situations.

BACKGROUND

Administering proper drug doses accurately and efficiently during an emergency or intensive care situation is of critical importance. This is particularly of essence in an emergency or critical care situation involving pediatric patients as even small dosing mistakes can lead to disastrous consequences. However, even under the best of circumstances and despite the best of efforts of medical personnel, inadvertent mistakes are sometimes made because of the multitude of steps involved in the drug administration process. More specifically, in a typical situation appropriate drug dosage must first be determined, which usually involves multi step mathematical calculations. This is followed by plurality of steps involved in the actual drug administration process, which may include selection of a correct medicine to be administered or medical dosing device to be used. Because each step carries with it a potential for introducing an error into the overall drug administration process, reducing the number of steps that must be executed can significantly increase the overall accuracy and efficiency of the process.

Drug dosages conventionally are determined based on the weight of the patient. However this method has been determined as being inappropriate and inaccurate especially in the emergency and critical care situations. First of all, a scale needed to determine the actual weight of the patient is often times not readily available in such circumstances or given the urgent nature of the situation the weight determination is simply not practical. Also, because a majority of the drugs administered in the emergency or critical care situations distribute only in the lean body tissue, basing drug dosages on the actual weight of the patient may lead to overdosing. Having recognized some of the shortcomings of the weight based dosing system, especially as related to the pediatric emergency or critical care situations have lead to development of a method for determining drug dosages based on the length of a patient.

In particular, one method that has been widely used, as it allows for a quick and efficient determination of drug dosages, involves the use of a color coded measuring tape for determining the length of a patient. More specifically, the Broselow® Pediatric Emergency Tape is a well known instrument that correlates easily obtainable patient length to drug dosages. The details of the instrument and the method of its use are disclosed in the U.S. Pat. Nos. 4,716,888 and 6,132,416 to Broselow which are incorporated by reference into the present disclosure. In general, the method involves measuring and coding patient length to one of the color zones provided on the tape and using the color-coded length to determine a drug dosage to be administered to the patient. By segmenting the tape into plurality of color coded zones rather than the typically used inches or centimeters, with each color zone corresponding to a given length range, the length of the patient can be easily read and noted as being of a certain color rather than as a specific measurement in centimeters or inches. In other words, each color-coded length zone corresponds to a certain, predetermined range of the actual lengths as measured in either metric or imperial units. For example, the grey color zone on the tape may correspond to a length range from 42.20 cm to 60.79 cm and the pink color zone on the tape may correspond to the length range from 60.80 cm to 67.79 cm. Thus, a patient whose length falls within the first length range would be coded as gray and a patient whose length falls within the second length range would be coded as pink. The appropriate drug dosages for the two patients would then be selected from a list of predetermined drug dosages listed on the tape.

Although the step of determining drug dosages has been greatly simplified with the use of aforementioned method, a number of other issues still remain that often lead to dosing errors or that make the medication administration process inefficient. For instance, in order to arrive at a correct dose of medicine that is to be administered once the medication dosage is determined a number of other calculations, such as those involving, for example, concentration of the medication, still need to be performed. Furthermore, the selection of a correct medicine, an appropriate medicine dosing device or drawing of a correct predetermined volume of medication into the medicine dosing device can each introduce an error or slow down the process of administering medication to the patient. Even in situations when medication dosages are based on dosing systems other than the conventional weight based systems, such as for example patient age, body surface area or volume, dosing inaccuracies may be observed due to the type of calibrations used in such systems. In particular, a typically used constant incremental change in dosages may result in a loss in needed dosing accuracy when such systems are used.

Thus, despite the availability of various techniques designed to simplify the process of drug dosage determination and administration, there still exists a possibility of errors because of the pressure of time and the environment under which the treatment is delivered, as well as the type of dosing systems that are being used. Accordingly, there is need for a device for, and method of, accurately and efficiently delivering drugs during an emergency or critical situation, especially to pediatric patients.

SUMMARY

A medicine dispensing device for administering a selected drug is disclosed herein. The medicine dispensing device includes a series of zones of varying widths marked on the surface of the medicine dispensing device, with each of the zones corresponding to a pre-determined dose of the drug that is correlated to one of the physical characteristics of a patient. The series of zones marked such that the smallest dose of the drug to be administered corresponds to a first zone that is proximate an opening through which the drug is to be dispensed.

A method for generating a dosing label for affixing to a medicine dispensing device is also disclosed. In one embodiment the method includes the steps of selecting a drug to be administered and determining drug doses for a plurality of color coded zones corresponding to one of the physical characteristics of a patient. The step of determining drug doses further comprising the steps of determining a concentration of the drug solution; determining a volumetric capacity of the medicine dispensing device; and calculating a width of individual color coded zones to be printed on the dosing label, with each individual color coded zone width corresponding to a drug dose based on one of the physical characteristics of the patient.

A method of administering drugs to patients more accurately and efficiently is disclosed herein. In one embodiment the method includes: determining a color coded zone for a patient from a plurality of color coded zones, the color coded zone corresponding to one of the physical characteristics of a patient; determining the drug to be administered to the patient; selecting a medical treatment kit including a container filled with the drug to be administered and a pre-marked medicine dispensing device, the pre-marked medicine dispensing device comprising a series of color coded zones of varying widths corresponding to drug doses that can be administered; determining a drug dose to be administered to the patient corresponding to the determined color coded zone; drawing medication from the container filled with the drug into the pre-marked medicine dispensing device to arrive at a color coded zone associated with the determined drug dose; verifying correctness of the drug dose, and administering the determined drug dose to the patient.

A method of administering drugs to patients more accurately and efficiently, may alternatively include the steps of: determining a color coded zone for a patient from a plurality of color coded zones, the color coded zone corresponding to one of the physical characteristics of a patient; determining the drug to be administered to the patient; selecting a prefilled and a pre-marked medicine dispensing device containing the drug, the prefilled and pre-marked medicine dispensing device comprising a series of color coded zones of varying widths corresponding to drug doses that can be administered; determining a drug dose to be administered to the patient corresponding to the determined color coded zone; expelling any excess medication from the prefilled and pre-marked medicine dispensing device to arrive at a color coded zone associated with the determined drug dose; verifying correctness of the drug dose remaining in the pre-filled and pre-marked medicine dispensing device; and administering the determined drug dose to the patient.

BRIEF DESCRIPTION OF THE DRAWINGS

FIG. 4 is flow diagram showing a method of determining and printing the color-coded medication dose labels.

FIG. 5 is flow diagram showing a method of administering a medication using the disclosed pre-filled and marked medicine-dosing device.

FIG. 7B illustrates the emergency medical treatment kit for administering a medication according to one embodiment of the current disclosure.

DETAILED DESCRIPTION

Figure 1A:
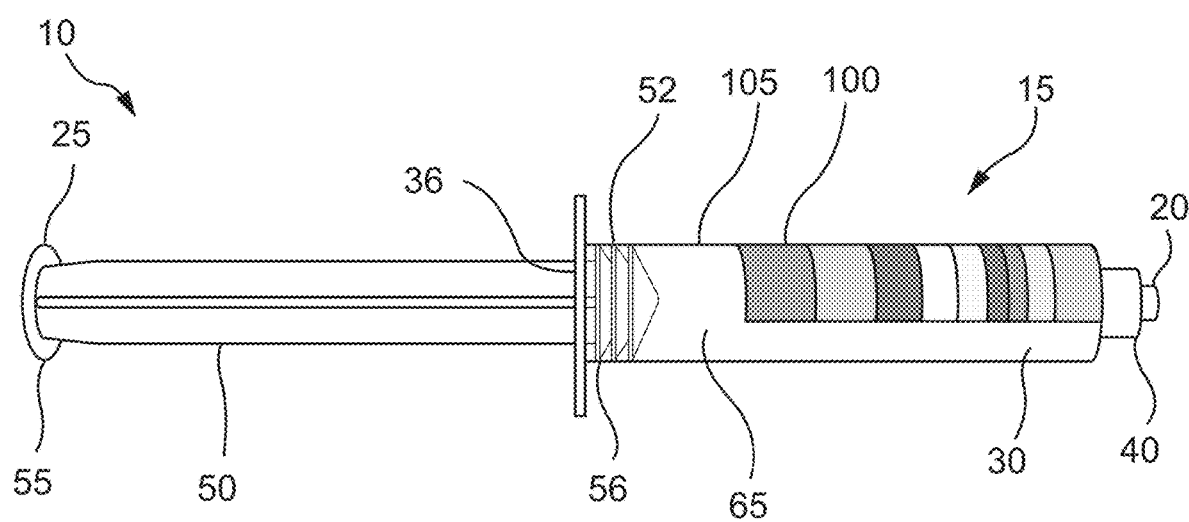
FIGS. 1A-1D are perspective views of a medicine-dosing device according to one embodiment of the current disclosure.

The present application describes a device and a method for administering proper medication doses to patients. In particular, a pre-marked medicine dosing/dispensing device designed to minimize medication dosing errors, as well as to improve the overall accuracy and efficiency of administering medication, especially in the emergency and critical care situations, is provided.

As discussed in detail below, in one embodiment the medicine dosing device 10 is a syringe 15 that includes an elongate barrel 30 marked with predetermined color-coded volumetric medicine doses 100 and a plunger 50. The medicine-dosing device, according to one embodiment, may be further pre-filled with a fluid 105 that corresponds to a medication to be administered to a patient. A method for determining specific volumetric doses for a plurality of medications based on different factors is also disclosed. In particular, according to one embodiment the method involves generating labels or marking medical dosing devices with doses that are determined based on, for example, volumetric capacity of medical dosing device and/or drug concentration.

Also, a method for administering proper medication doses using the pre-marked medicine-dosing device is discussed. The method disclosed leads to a significant reduction in the amount of time required to determine and administer a dose of medication to a patient and at the same time decreases the risk that such doses will be miscalculated or otherwise erroneously administered.

Device

For a detailed discussion of the first embodiment of the pre-labeled medicine dosing/dispensing device 10, reference is now made to FIGS. 1A-1D. As shown in FIG. 1A, the medicine dosing device 10 according to one embodiment is a syringe 15 that includes a proximal end 25 and a distal end 20 opposite the proximal end. The syringe includes a vessel, such as a syringe barrel 30 at the distal end for holding therein a medicine that is to be dispensed, and a plunger 50 that extends proximally from an opening 36 located at the proximal end 35 of the syringe barrel to the proximal end 55 of the plunger at the proximal end 25. The syringe barrel and plunger are both manufactured from material such as plastic, glass or any other suitable transparent medical grade material that is inert or will not disrupt the chemical balance of the fluid inside.

Figure 1B:
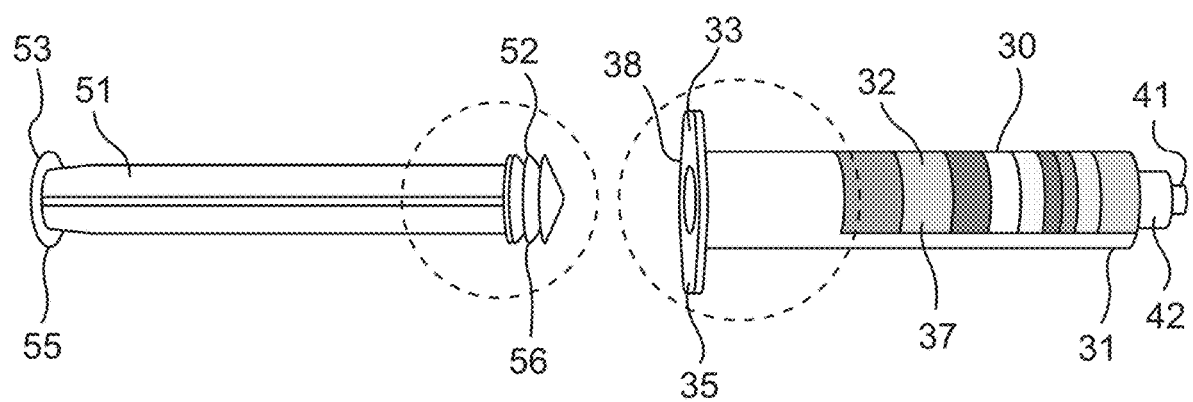
Figure 1C:
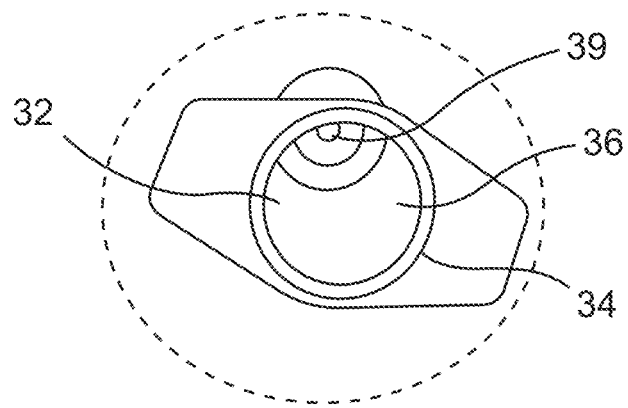
Figure 1D:
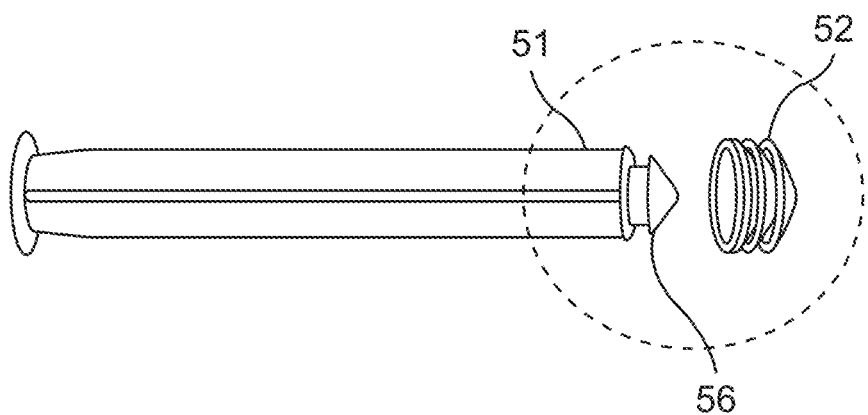

As illustrated in FIG. 1B the syringe barrel 30 is elongate and substantially cylindrical and includes a distal end 31 and a proximal end 35. The syringe barrel further includes and outer circumferential surface 37 and an inner circumferential surface 38. A chamber 32 capable of receiving a plunger and retaining a fluid therein is defined by the inner circumferential surface 38 of the barrel between the distal and proximal ends 31 and 35. A flange 33, which can serve as a finger grip to provide for an easier handing of the syringe, is integrally formed with the proximal end of the barrel and defines an opening 36 for receiving the plunger. Proximate the opening 36, along the inner surface of the barrel, is a ridge 34, shown in FIG. 10, that prevents the plunger from slipping out of the barrel once it is engaged with the barrel.

The opening 36 is in communication with the chamber 32 and an orifice 39 located at the distal end 20 of the syringe barrel. A tip 40 for attaching a needle, nozzle or tubing for expelling the liquid contained within the syringe barrel 30 is integrally formed with the distal end 20 of the barrel and in communication with the orifice 39. The tip may include coaxially positioned inner 41 and outer 42 members. According to one embodiment the tip may include a Luer taper fitting.

The plunger 50, according to one embodiment shown in FIG. 1B, includes a plunger rod 51 and a rubber or plastic gasket or stopper 52 attached to the distal end 56 of the plunger rod. The gasket forms a tight seal between the inner surface of the barrel and the plunger in order to prevent the contents of the syringe from escaping out the back of the syringe. An annular flange 53 is integrally formed with the proximal end 55 of the plunger rod. The plunger 50 has an elongate shape complementary to that of the chamber 30 and is designed such that it can be pushed along the chamber (inside of the cylindrical barrel or tube) allowing the syringe to expel fluid through the tip 40 or orifice 39 at the distal end of the barrel. Alternatively the plunger can include any other configuration capable of forcing the fluid from inside the chamber 30 through the tip 40 or orifice 39.

According to one embodiment of the present disclosure, the medicine dosing device may be prefilled with a pre-selected drug. Initially, when the medicine dosing device is prefilled and the syringe is in the pre-medication administration position, the substantial length of the plunger rod extends longitudinally outside of the syringe barrel. In other words, as shown in FIG. 1A, prior to the administration of the medicine, only the gasket 52 and the distal end 56 of the plunger rod are initially inside the syringe barrel, at the proximal end 35 of the barrel, with the remaining part of the plunger length outside of the barrel such that its proximal end 55 is in its most extended configuration. Alternatively, in an instance when the medicine dosing device comes as a part of a kit that requires for the drug provided in an included medicine vessel to be drawn into the medicine dosing device immediately prior to the drug administration process, the plunger rod may remain inside the syringe barrel until the drug is drawn into the syringe.

Figure 2A:
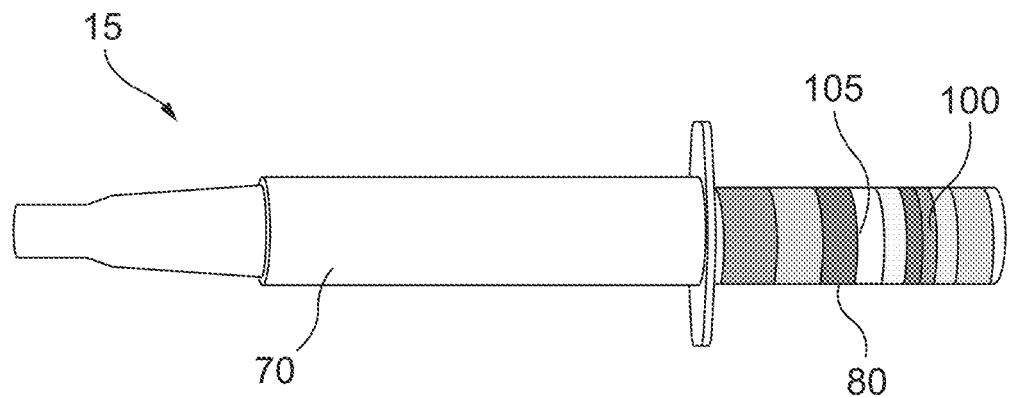
FIGS. 2A-2D are perspective views of a medicine-dosing device according to another embodiment of the current disclosure.
Figure 2B:
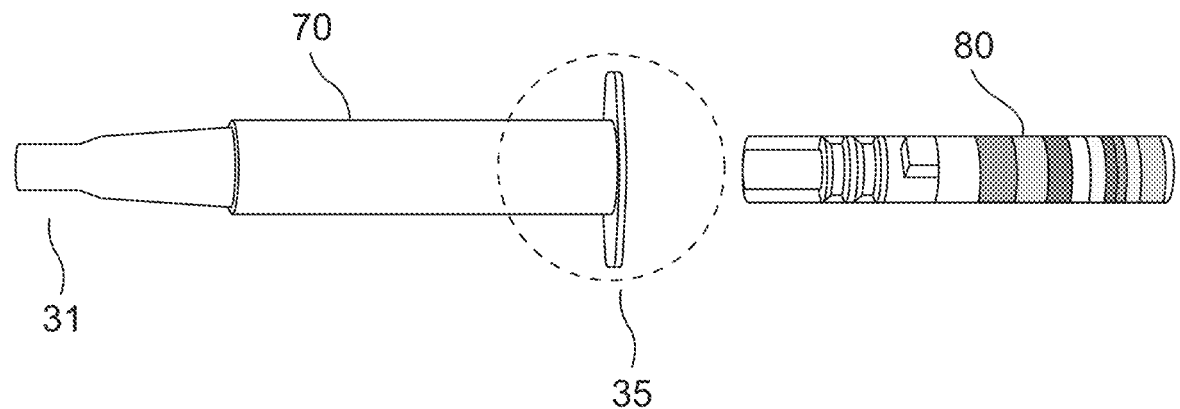
Figure 2C:
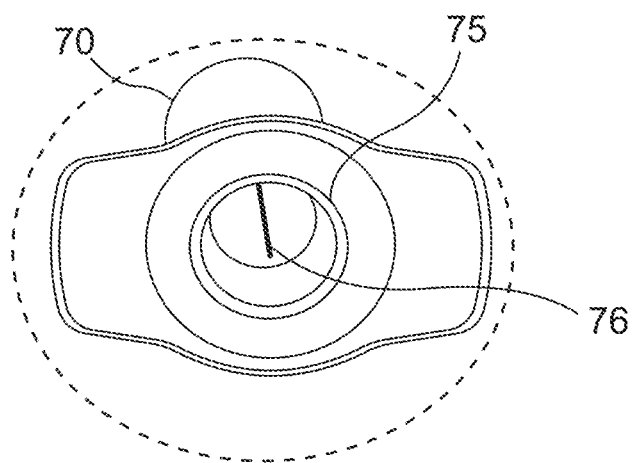
Figure 2D:
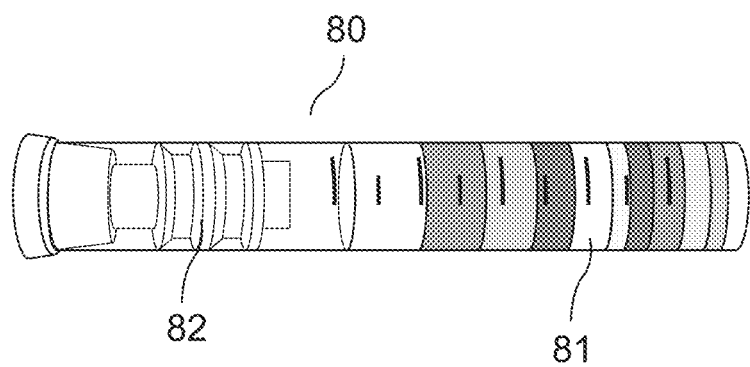

According to another embodiment shown in FIG. 2A, syringe 15 may include an elongate barrel 70 and a plunger 80 marked with predetermined color-coded volumetric medicine doses 100 and prefilled with a fluid 105 that corresponds to a medication to be administered to a patient. In this configuration, as illustrated in FIG. 2C the syringe barrel includes an inner tubular body 75 that is generally coaxially aligned with the larger diameter of the cylindrical barrel. The inner tubular body has a needle 76 coaxially positioned within the inner tubular body and longitudinally aligned with the inner tubular body. The plunger 80, shown in FIG. 2D, includes a substantially cylindrical member or vial 81 and a stopper 82. Because the syringe barrel and the plunger are initially separated, as shown in FIG. 2B, prior to the administration of the medication, the plunger 80 needs to be inserted into the proximal end 35 of the syringe barrel, such that the stopper 82 fully engages with the inner tubular body 75 and the needle 76.

According to yet another embodiment of the current disclosure the plunger and/or plunger stopper can be color coded based on the medication contained in the barrel. Such color coding of the plunger can further increase efficiency with which medication is administered and can make the administration even less error prone as visual inspection of the plunger can provide a quick verification of the correctness of the medication to be administered.

Alternatively the medicine dosing device can include any vessel, such as for example tube, vial, bag or bottle, capable of containing therein and expelling therefrom a desired medicine. For example, the medicine dosing device could be a bag containing an IV fluid. According to this embodiment, the bag may be marked with a series of color coded zones along with the traditional volume markings. When used in combination with the traditional volume markings, the color coded zones could serve as a reminder to the medical personnel of a correct volume of each medication that can be given to a patient based on the patient's color zone. The color coded zones may also be used as a key for entering a correct total volume to be dispensed into the IV pump for a given medication.

The description will now turn to the markings on the surface of the medicine dosing device. In case of a syringe, the markings may be placed along a circumferential surface of the syringe barrel or plunger. As shown in FIGS. 1 through 3, the markings include a series of substantially translucent bands or zones 100 indicative of the possible medicine doses to be administered to a patient. Although the markings shown in the figures include a series of color coded zones, the markings could also include zones with different patterns, textures, etc. Regardless of the type of the marking used, the markings are either directly imprinted, painted, etched or stained on an inside or outside surface of the medicine dosing device or a label or sleeve may be generated that can be affixed or placed over the outer surface of the medicine dosing device. The applied markings are such that the fluid level, once the device is filled, can be easily seen through the markings.

Figure 3A:
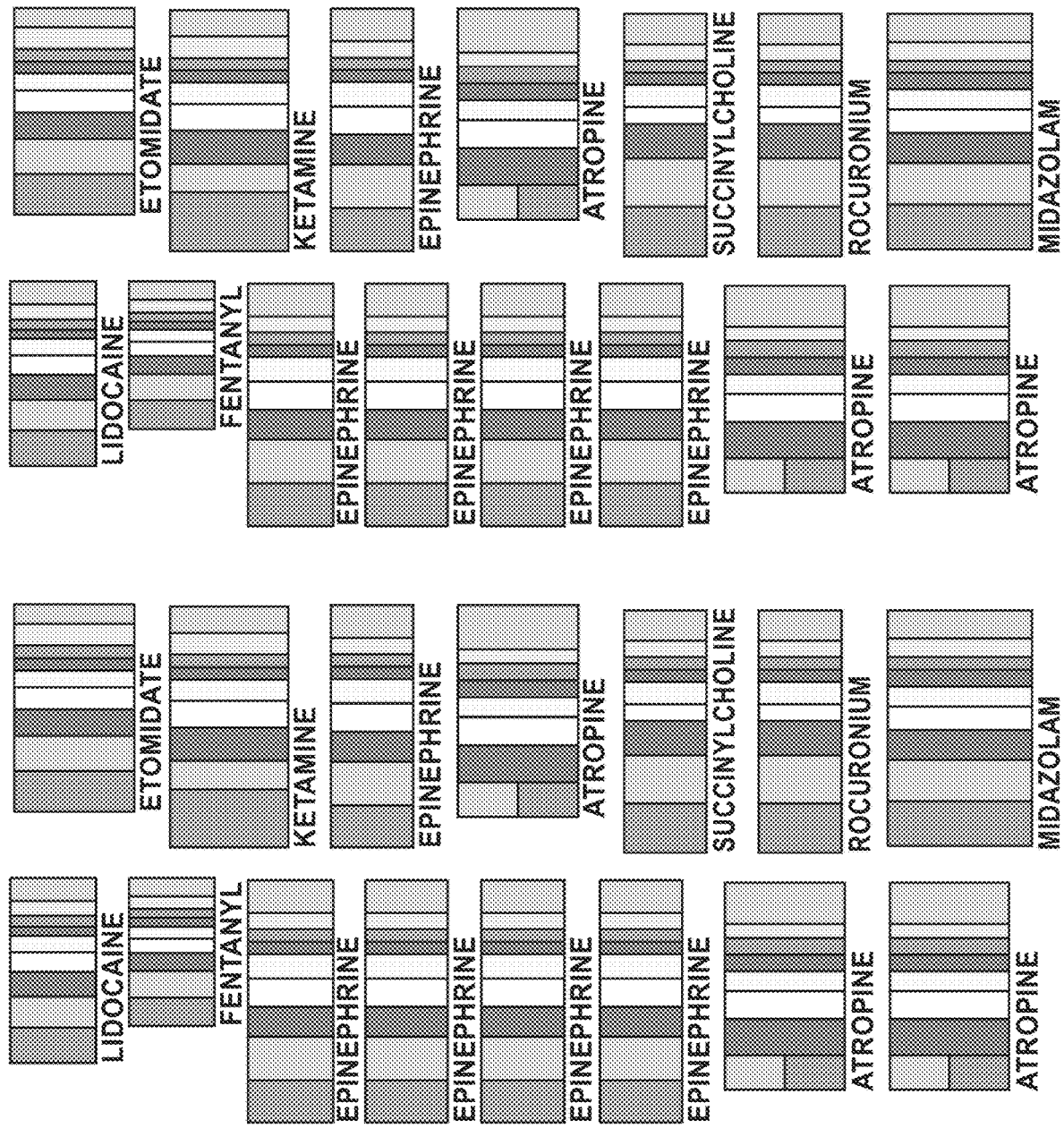
FIGS. 3A-3D are plan views of the labels with the color-coded medication doses.

FIG. 3A shows a plurality of labels in accordance with one embodiment of the current disclosure. Each label 300 is substantially rectangular in shape and is sized based on the volumetric capacity of the medical dosing device to which the label is to be affixed. In other words, because of the volumetric variations among the medicine dosing devices and as a result of variations in the circumferential outer surface of such devices, the size or dimensions of the label is adjusted accordingly to ensure that it properly covers the outer surface of the of the medical dosing device. For example, when labels are made for syringes with two different volumetric barrel capacities, the label size is either increased or decreased in both length and width to accommodate for the changes in the outer surface of the barrel.

Figure 3B:
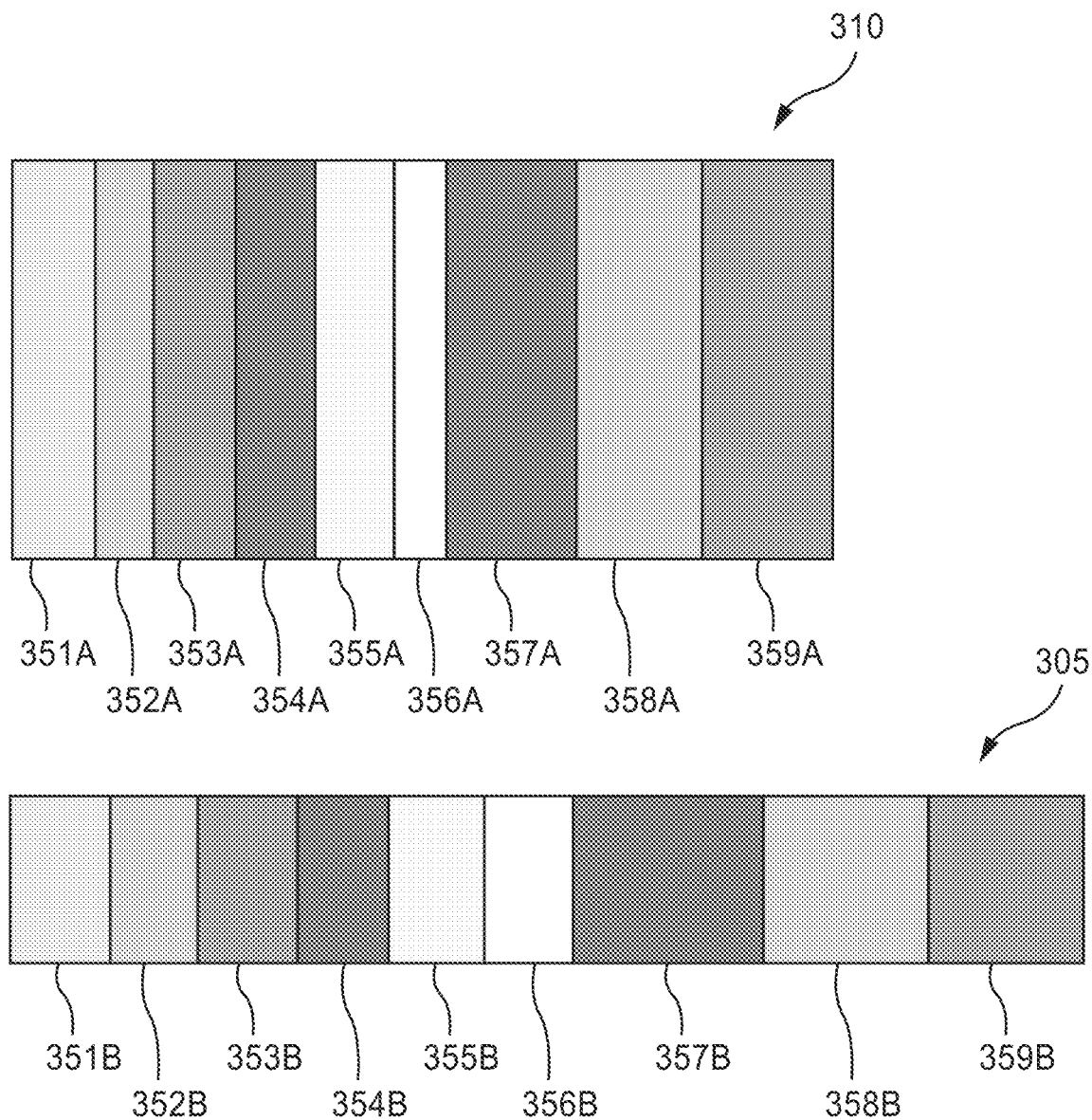

Along with the changes in the label size, appropriate corresponding changes to the widths of the color bands or zones that are printed on the label are also made based on medicine dosing device used to dispense the medication. More specifically, in order to take into account the variations in the volume of a medicine-dispensing device, the changes to the widths of the color bands or zones need to be made in order to maintain the same volumetric dose of medicine across various medicine dispensing devices. For example, as shown in FIG. 3B, labels for the same medicine loaded into a 10 cc medicine dispensing device and 5 cc dispensing device have two different widths for each color band or zone in order to keep the medicine doses the same for both medicine dosing devices. In other words, in order to dispense the same amount of medication using a 10 cc dispensing device as compared to using a 5 cc dispensing device, the width of the color bands 351A-359A on the label 310 for the 10 cc device would be smaller than the color bands 351B-359B on the label 305 for the 5 cc dispensing device in order to deliver the same amount of medication to the patient.

Similarly, the concentration of the medication that is used also affects the widths of the color bands or zones printed on the label. More specifically, the widths of the color bands or zones are determined based on the concentration of the medication, with the medication at a higher concentration corresponding to a smaller volumetric dose, or smaller band width, than the medication at a lower concentration.

Figure 3C:
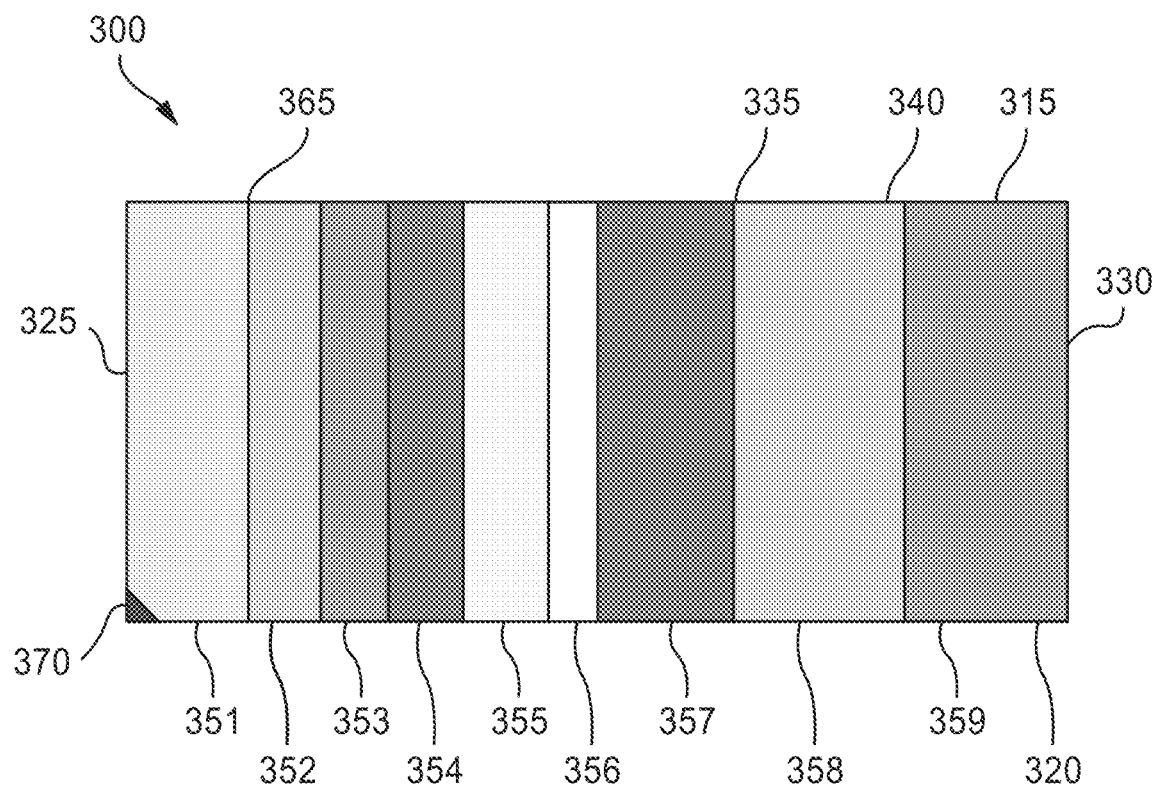

As depicted in FIG. 3C the label 300 has opposing parallel sides 315 and 320 and opposing parallel ends 325 and 330 and includes a series of consecutive color bands or zones 351 through 359 of varying widths that correspond to the medication doses for each of the color coded patient length ranges discussed above. More specifically, each color band has a width that is defined by leading 335 and trailing 340 edges that are parallel to the opposing ends 325 and 330 of the label and which, once the label is affixed to the medicine dispensing device, corresponds in volume to a predetermined dose of medicine appropriate for the patient whose length or any other physiological characteristic of a patient that falls within a predefined color-coded range. In other words, each color band or zone on the label represents a medication dose correlated to respective color-coded length range or other physiological characteristic.

Still referring to FIG. 3C, according to one embodiment, nine distinct color bands 351-359 can be used to distinguish between nine different doses of medication corresponding to nine distinct color coded patient length ranges. More specifically, each of the colors corresponds to one of nine different dosages of a specific medication. As shown in the FIG. 3C, in one particular implementation, band colors may include grey 351, pink 352, red 353, purple 354, yellow 355, white 356, blue 357, orange 358 and green 359, with the grey color band corresponding to the smallest dose of the medication and the green color band corresponding to the largest dose of medication that can be delivered. A solid black lines 365 may be utilized at the boundaries between the various color bands or zones to facilitate the process of drug administration as will be discussed in more detail below. Although, the discussion will be made with reference to the specific colors shown in the FIGS. 3A-3C, it can be readily appreciated that other colors or markings may be used. Alternatively, color names may be printed within the band or zone widths in addition to or instead of colors.

Figure 3D:
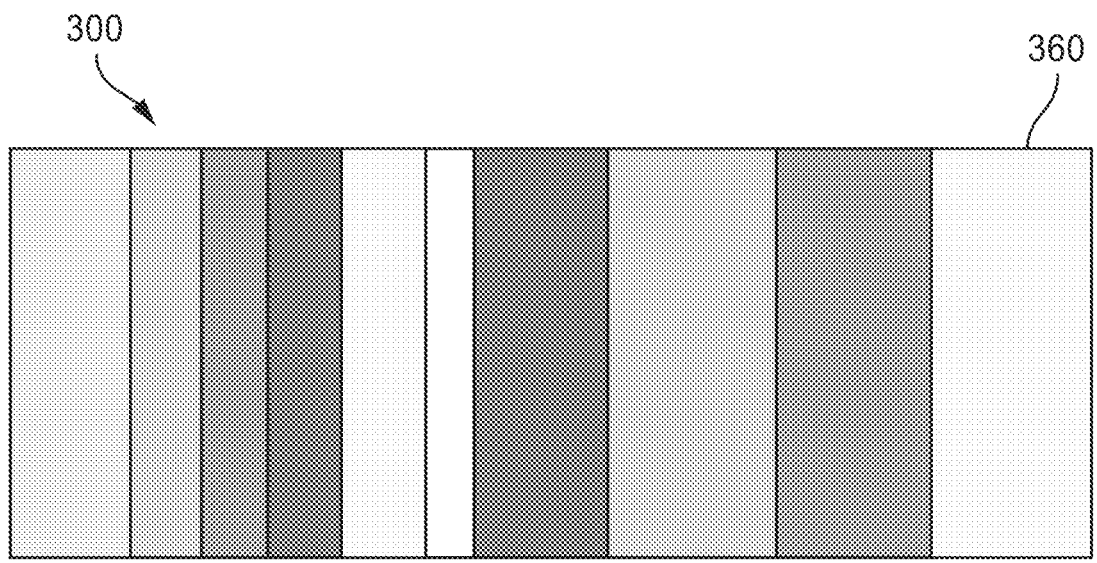

According to yet another embodiment shown in FIG. 3D, a label may include ten different bands of colors with the tenth band 360 corresponding to the largest dose of medication that can be delivered. In this particular embodiment the largest dose can correspond to the universal dose that can be delivered to any patient whose length falls outside of the previously disclosed colored length ranges. For example, the universal label in accordance with this embodiment can be applied to the universal medicine-dosing device that can be used for both pediatric and adult patients and as such eliminates a need for having two separate medicine dosing systems for the two distinct patient groups. Although, in the examples provided above a specific number of color bands have been discussed, it should be noted that any number of color bands that allow for more precise medicine dosing can be used. For example, in some cases, if needed the previously defined bands or zones can be further subdivided into sub-band or sub-zone to allow for a more precise medicine dosing.

Also, in accordance with another embodiment of the current disclosure, and as shown in FIG. 3C one of the label edges can include a mark 370 that would help ensure that the label is correctly affixed or positioned on the syringe or plunger. For example, the label edge that is to be aligned with the distal end of the syringe barrel can be marked in order to prevent affixing the label to the barrel in the reverse direction, and thus leading to the incorrect doses being administered at a later time. For example, the edge of the label with the color band corresponding to the smallest dose can include a mark at its leading edge that facilitates the alignment of the label with a distal end of the syringe barrel.

Furthermore, in accordance with another embodiment as shown in FIG. 3A, the label may include the name of the medication that is to be administered or any other information that maybe important to ensuring that a correct medication would be administered to the patient. In particular, the name of the medication can be imprinted along the length of the label or any other position as long as it provides for an easy verification of the correctness of the medicine in the medicine-dosing device.

Method of Determining and Generating Dosing Information

The discussion will now turn to a method 400 for determining the medicine doses for a plurality of medications and medicine dispensing devices. In one particular example, shown in FIG. 4, the method may culminate in generating of a color-coded dose label that can be applied to a selected medical dosing device. As shown in FIG. 4, the method 400 begins at step 401 during which the selection of the medicine for which the dosing label is to be generated is made. As related to emergency or critical care situation some of the most commonly used medications include, for example, atropine, lidocaine, fentanyl, epinephrine, etomidate, ketamine, succinylcholine, rocuronium, and midazolam to name a few. However, it should be appreciated that the method can be equally applied to any other medication that can be administered using the disclosed medicine dispensing device. Once the medication for which a label is to be generated is identified, the doses of the drug for each of the color coded length zones previously discussed is determined at step 402. Table 1 below provides dosages in mg for some of the above listed drugs. As can be seen in Table 1, the dosages for each drug differ not only based on the type of the drug but also based on the length of the patient. Thus, for example, as shown in Table 1, a dose for a patient falling within the yellow color-coded length zone is 16 mg for succinylcholine and 13 mg for rocuronium. In case the same drug is to be administered to two different patients whose length falls within different color coded lengths, two different medication doses would be used as shown. For example, in the case of epinephrine, with one of the patient lengths being coded as red and the other as blue, the dose of medication to be administered to each patient would be 0.085 mg and 0.21 mg, respectively. Alternatively, doses of the drug may be determined based on dosing recommendations other than those based on the length of the patient.

After the dose to be administered to the patient is determined at step 402, the drug concentration for the drug selected in step 401 is then determined at step 403. The concentration of the drug is directly related to the volume that needs to be administered. In other words, a smaller volume of the same medication needs to be administered for a solution with a higher concentration than for a solution with a lower concentration.

The next step, step 404, involves selection of a medicine dispensing device to which the label is to be applied. As described above, because medicine dispensing devices come in various volumetric sizes, a medicine dispensing devices conversion factor that is based on the length and width of the medicine dosing device and/or the concentration of the medication may be used to take into account the variations in size and/or shape of different medicine dispensing devices for which the label is to be generated. Thus, once the medicine dispensing device of a particular volume is selected for administering the selected medication, a corresponding conversion factor listed in Table 1 can be used in order to calculate both the individual color band/zone widths and a total band widths that correspond to the determined medication doses (step 405). More specifically, the width of each color band/zone that corresponds to the determined medication dose is calculated based on the dose of the drug to be administered, the solution concentration and medicine dispensing device volumetric capacity. According to one embodiment all of the calculations may be performed by a computer processing unit (CPU) in response to a user provided input.

Applying of the label to the medicine dosing device may take place once the width of each color band or zone is determined and the label is printed. For instance, when the label is to be applied to a syringe having a barrel and a plunger, with the barrel designed for holding the medicine that is to be dispensed, the label may be place along the outer circumferential surface of the barrel by aligning one of the edges of the label that corresponds to a color band of the smallest dosing with the distal edge of the syringe barrel of the medicine dispensing device 10. Alternatively, in a syringe in which a plunger serves as a vessel for holding the medicine, the label may be placed along the outer circumferential surface of the plunger by aligning one of the edges of the label that corresponds to a color band of the smallest dosing with the proximal end of the medicine dosing device.

Although the pre-calculated band/zone widths for each of the selected medication, medicine dispensing device volumetric capacity and solution concentration may be printed on a label that can be applied to the medicine dispensing device, the dosing information may also be directly imprinted, etched, stained or painted on the medicine dispensing device. Alternatively, the dosing information can be printed on a sleeve that can be placed over the medicine dispensing device.

Depending on the embodiment, the appropriately labeled medicine-dosing device may be prefilled with a desired medication, with the fluid volume corresponding to the maximum dose that can be administered to the patient whose, for example, length falls within the maximum length zone. When the medicine dosing unit is prefilled with the selected medication the label can be applied either before or after the medicine dosing device is filled. In case the medicine dosing device is filled with a selected medication immediately prior to the medication administration process, as might be the case when the medicine dosing device is included as a part of a kit that includes the medical dosing device and a vessel filled with a drug to be administered, an empty pre-labeled medicine dosing device is supplied for use. Accordingly, a fluid volume that corresponds to a predetermined dose for a given patient may be drawn into the pre-labeled medicine dosing device from the container immediately prior to drug administration.

TABLE 1

| Drug | Color-Coded Length | Dose (mg) | Concentration (mg/ml) | Medicine Dosing Device (cc) | Conversion Factor (mm/cc) | Color band or zone width (mm) | Total Distance (mm) |
|---|---|---|---|---|---|---|---|
| Epinephrine | Gray | 0.04 | 0.1 | 3 | 16 | 6.4 | 6.4 |
| | Pink | 0.065 | 0.1 | 3 | 16 | 4 | 10.4 |
| | Red | 0.085 | 0.1 | 3 | 16 | 3.2 | 13.6 |
| | Purple | 0.1 | 0.1 | 3 | 16 | 2.4 | 16 |
| | Yellow | 0.13 | 0.1 | 3 | 16 | 4.8 | 20.8 |
| | White | 0.17 | 0.1 | 3 | 16 | 6.4 | 27.2 |
| | Blue | 0.21 | 0.1 | 3 | 16 | 6.4 | 33.6 |
| | Orange | 0.27 | 0.1 | 3 | 16 | 9.6 | 43.2 |
| | Green | 0.33 | 0.1 | 3 | 16 | 9.6 | 52.8 |
| Fentanyl | Gray | 12 | 50 | 3 | 16 | 3.84 | 3.84 |
| | Pink | 20 | 50 | 3 | 16 | 2.56 | 6.4 |
| | Red | 25 | 50 | 3 | 16 | 1.6 | 8 |
| | Purple | 32 | 50 | 3 | 16 | 2.24 | 10.24 |
| | Yellow | 40 | 50 | 3 | 16 | 2.56 | 12.8 |
| | White | 50 | 50 | 3 | 16 | 3.2 | 16 |
| | Blue | 63 | 50 | 3 | 16 | 4.16 | 20.16 |
| | Orange | 80 | 50 | 3 | 16 | 5.44 | 25.6 |
| | Green | 100 | 50 | 3 | 16 | 6.4 | 32 |
| Midazolam-RSI | Gray | 1.2 | 1 | 12 | 5.16 | 6.192 | 6.129 |
| | Pink | 2 | 1 | 12 | 5.16 | 4.128 | 10.32 |
| | Red | 2.5 | 1 | 12 | 5.16 | 2.58 | 12.9 |
| | Purple | 3.2 | 1 | 12 | 5.16 | 3.612 | 16.512 |
| | Yellow | 4 | 1 | 12 | 5.16 | 4.128 | 20.64 |
| | White | 5 | 1 | 12 | 5.16 | 5.16 | 25.8 |
| | Blue | 6.3 | 1 | 12 | 5.16 | 6.708 | 32.508 |
| | Orange | 8 | 1 | 12 | 5.16 | 8.772 | 41.28 |
| | Green | 10 | 1 | 12 | 5.16 | 10.32 | 51.6 |
| Ketamine | Gray | 6.75 | 10 | 6 | 8 | 5.4 | 5.4 |
| | Pink | 13 | 10 | 6 | 8 | 5 | 10.4 |
| | Red | 17 | 10 | 6 | 8 | 3.2 | 13.6 |
| | Purple | 20 | 10 | 6 | 8 | 2.4 | 16 |
| | Yellow | 26 | 10 | 6 | 8 | 4.8 | 20.8 |
| | White | 33 | 10 | 6 | 8 | 5.6 | 26.4 |
| | Blue | 42 | 10 | 6 | 8 | 7.2 | 33.6 |
| | Orange | 50 | 10 | 6 | 8 | 6.4 | 40 |
| | Green | 66 | 10 | 6 | 8 | 12.8 | 52.8 |

TABLE 1-continued

| Drug | Color-Coded Length | Dose (mg) | Concentration (mg/ml) | Medicine Dosing Device (cc) | Conversion Factor (mm/cc) | Color band or zone width (mm) | Total Distance (mm) |
|---|---|---|---|---|---|---|---|
| Etomidate | Gray | 0.9 | 2 | 5 | 9 | 4.05 | 4.05 |
|  | Pink | 2 | 2 | 5 | 9 | 4.95 | 9 |
|  | Red | 2.5 | 2 | 5 | 9 | 2.25 | 11.25 |
|  | Purple | 3.2 | 2 | 5 | 9 | 3.15 | 14.4 |
|  | Yellow | 4 | 2 | 5 | 9 | 3.6 | 18 |
|  | White | 5 | 2 | 5 | 9 | 4.5 | 22.5 |
|  | Blue | 6.3 | 2 | 5 | 9 | 5.85 | 28.35 |
|  | Orange | 8 | 2 | 5 | 9 | 7.65 | 36 |
|  | Green | 10 | 2 | 5 | 9 | 9 | 45 |
| Atropine | Gray | 0.1 | 0.1 | 5 | 9 | 9 | 9 |
|  | Pink | 0.13 | 0.1 | 5 | 9 | 2.7 | 11.7 |
|  | Red | 0.17 | 0.1 | 5 | 9 | 3.6 | 15.3 |
|  | Purple | 0.21 | 0.1 | 5 | 9 | 3.6 | 18.9 |
|  | Yellow | 0.26 | 0.1 | 5 | 9 | 4.5 | 23.4 |
|  | White | 0.33 | 0.1 | 5 | 9 | 6.3 | 29.7 |
|  | Blue | 0.42 | 0.1 | 5 | 9 | 8.1 | 37.8 |
|  | Orange | 0.5 | 0.1 | 5 | 9 | 7.2 | 45 |
|  | Green | 0.5 | 0.1 | 5 | 9 | 0 | 45 |
| Succinylcholine | Gray | 8 | 20 | 3 | 16 | 6.4 | 6.4 |
|  | Pink | 13 | 20 | 3 | 16 | 4 | 10.4 |
|  | Red | 17 | 20 | 3 | 16 | 3.2 | 13.6 |
|  | Purple | 20 | 20 | 3 | 16 | 2.4 | 16 |
|  | Yellow | 26 | 20 | 3 | 16 | 4.8 | 20.8 |
|  | White | 30 | 20 | 3 | 16 | 3.2 | 24 |
|  | Blue | 40 | 20 | 3 | 16 | 8 | 32 |
|  | Orange | 53 | 20 | 3 | 16 | 10.4 | 42.4 |
|  | Green | 66 | 20 | 3 | 16 | 10.4 | 52.8 |
| Rocuronium | Gray | 4 | 10 | 3 | 16 | 6.4 | 6.4 |
|  | Pink | 7 | 10 | 3 | 16 | 4.8 | 11.2 |
|  | Red | 9 | 10 | 3 | 16 | 3.2 | 14.4 |
|  | Purple | 10 | 10 | 3 | 16 | 1.6 | 16 |
|  | Yellow | 13 | 10 | 3 | 16 | 4.8 | 20.8 |
|  | White | 16 | 10 | 3 | 16 | 4.8 | 25.6 |
|  | Blue | 21 | 10 | 3 | 16 | 8 | 33.6 |
|  | Orange | 27 | 10 | 3 | 16 | 9.6 | 43.2 |
|  | Green | 33 | 10 | 3 | 16 | 9.6 | 52.8 |
| Lidocaine-RSI | Gray | 6 | 20 | 3 | 16 | 4.8 | 4.8 |
|  | Pink | 10 | 20 | 3 | 16 | 3.2 | 8 |
|  | Red | 13 | 20 | 3 | 16 | 2.4 | 10.4 |
|  | Purple | 15 | 20 | 3 | 16 | 1.6 | 12 |
|  | Yellow | 20 | 20 | 3 | 16 | 4 | 16 |
|  | White | 25 | 20 | 3 | 16 | 4 | 20 |
|  | Blue | 32 | 20 | 3 | 16 | 5.6 | 25.6 |
|  | Orange | 40 | 20 | 3 | 16 | 6.4 | 32 |
|  | Green | 50 | 20 | 3 | 16 | 8 | 40 |

Method of Administering Drugs

Figure 6:
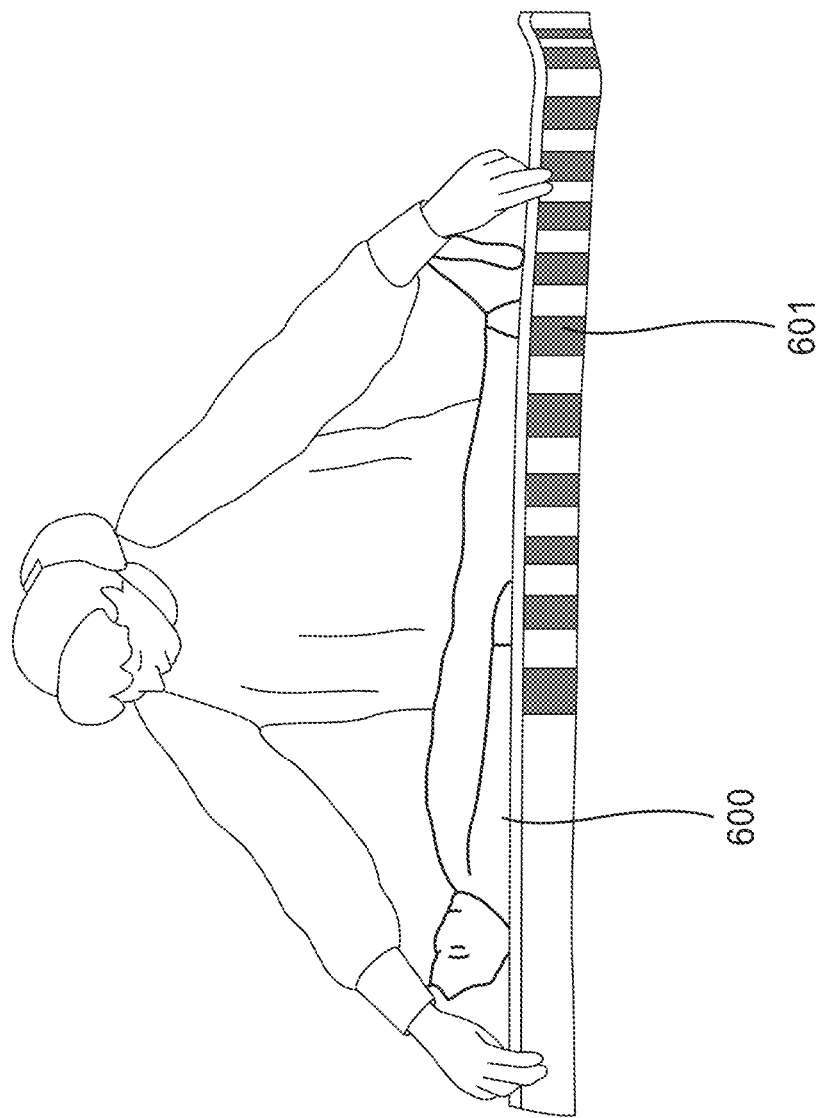
FIG. 6 illustrates a measuring instrument used to determine a color-coded length of a patient.

The medicine dosing device assembled according to the steps discussed above may be used to safely and efficiently deliver drugs. FIG. 5 is a flow diagram 500 of a method for administering drugs to a patient using the disclosed medicine dosing device 10 according to one embodiment. In this particular example, the disclosed method provides steps for efficiently administering a selected medicine to a patient from a prefilled and pre-marked medicine dosing device. As shown in the figure, the method begins at step 501 at which a color-coded length or any other physical characteristic of the patient is determined. In case of the length, a Broselow tape or any other similar type of instrument that provides color-coded length ranges can be used at this step. As shown in FIG. 6, the color coded length may be obtained by placing a patient 600 along the tape 601 and noting the color-coded length of the patient on the tape. Alternatively, any other physiological characteristic, such as for example, body surface area or volume, that can be color coded and correlated to medication dosages can be used. Once the patient length or any other physiological characteristic is determined and/or coded to a specific color range, a prefilled medicine dispensing device 10 containing medication to be administered is selected at step 502. The medication selection is verified by either reading the name of the medication imprinted along the outer surface of the pre-filled medicine dispensing device or by verifying the color of the plunger rod as discussed above. After the color code for the patient length is determined and noted, and the correctness of the medicine to be administered is verified, the appropriate dose of medication to be dispensed or its corresponding volume is then determined at step 503. For example, if the patient length is determined as falling within the blue color range on the measuring tape, the volume of medication to be administered to the patient will be the volume corresponding to the blue color band or zone on the medicine dosing device. Thus, because the medicine dispensing unit is prefilled with medication, the appropriate dose of medicine can be obtained by purging any excess of medication from the prefilled syringe until a desired volume of the medication is reached as indicated in step 504. In other words, with the prefilled volume corresponding to the maximum dose that can be administered to the patient, unless the patient length is determined to fall within the range of the maximum possible dose, some of the medication has to be purged from the prefilled medicine-dosing device prior to administering of the drug. Thus, according to one embodiment the plunger is pushed along the inside of the barrel toward the distal end 31 of the barrel until the proximal end of the plunger 54 is aligned with the solid line at the boundary between two different bands or zones, which corresponds to the trailing edge of a desired dosing band or zone. For example, in case of the above mentioned patient whose length was coded as being blue, with the blue band having a leading edge proximate the distal end of the barrel and the trailing edge proximate the proximal end of the barrel, the plunger is pushed toward the distal end of the barrel until the distal end of the plunger is aligned with the trailing edge of the blue band. Once all the excess fluid is purged from the prefilled dosing device per step 504, the correctness of the medicine dose is verified at step 505 and the medicine is then administered to the patient at step 506.

Figure 7A:
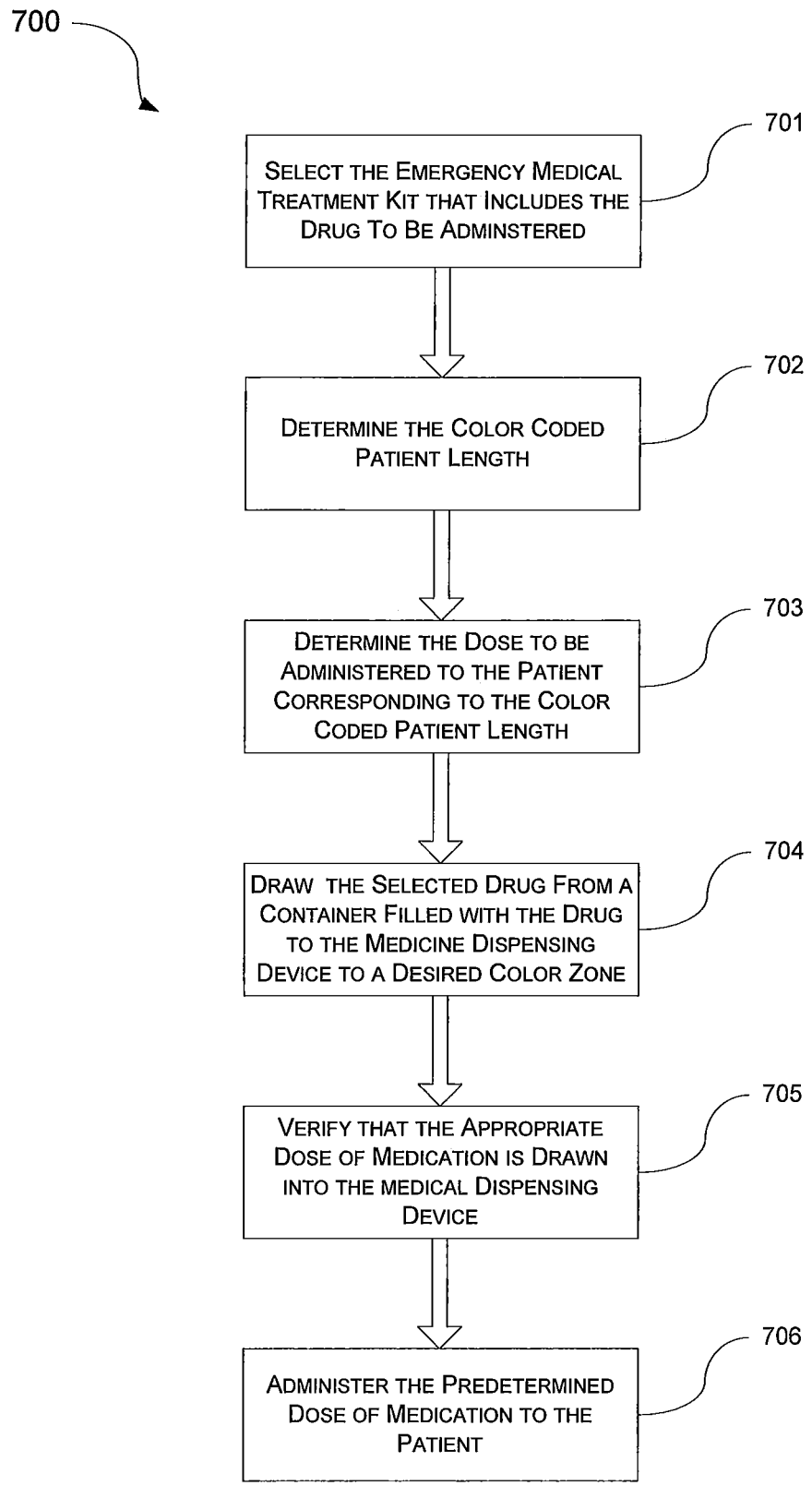
FIG. 7A illustrates a method of administering a medication using the disclosed emergency medical treatment kit that includes the pre-marked medicine dosing device.

Alternatively, according to another embodiment, the medicine-dosing device can be used to administer drugs to patients following the method shown in FIG. 7A. In particular, the method for administering drugs can begin with the selection of an emergency medical treatment kit that includes a drug to be administered to the patient (step 701). As shown in FIG. 7B, the medical treatment kit may include a container, such as box, bag, pouch or any other suitable container capable of holding the medicine dosing device therein, labeled on the outside surface with the name of the medication contained in the container among other things. For example, according to one embodiment, in addition to having the name of the drug listed on the label, the label may also include information on the concentration of the drug and/or instruction on how to use the kit to administer the drug. The medical treatment kit may further include a pre-marked medicine dosing device, such as for example a syringe, with the color-coded zones calibrated to the different drug doses for the selected drug. The syringe markings may also include the name of the drug that is to be delivered or any other information that may be helpful in ensuring that the drug is correctly delivered to the patient. The medical treatment kit may also include a needle, such as a blunt filling needle that can be plastic or made of any other suitable material, for facilitating drawing of the drug into the syringe. The medical treatment kit may also contain a container, such a bottle, vial, etc, for holding the drug that is labeled with the drug name on the outside of the container. The container may include a stopper or a lid that helps to contain the drug inside the container. The stopper or lid may be made from, for example, rubber or any other suitable material that can be easily punctured with the filling needle, such that the drug from the container can be easily drawn into the medicine-dosing device.

In case drug doses are based on patient's length, the color-coded length of the patient may be determined (step 702) using an instrument such as a Broselow tape or any other similar type of device that provides color-coded length ranges as discussed above with reference to FIG. 6. Appropriate volume of the drug to be administered may be subsequently determined based on the color-coded patient length (step 703). The determined drug volume may be then drawn into the medicine-dosing device (step 704). In particular, the drug may be drawn into the medicine-dosing device until the desired color zone on the medicine-dosing device is reached. Once the appropriate dose of the drug is drawn into the medicine-dosing device and verified (step 705) the drug can then be administered to the patient (step 706). According to one embodiment as shown in FIG. 7B, when the medicine-dosing device is a syringe with a pre-attached filling needle, the filling needle might be disposed off prior to the administration of the medication.

Figure 8A:
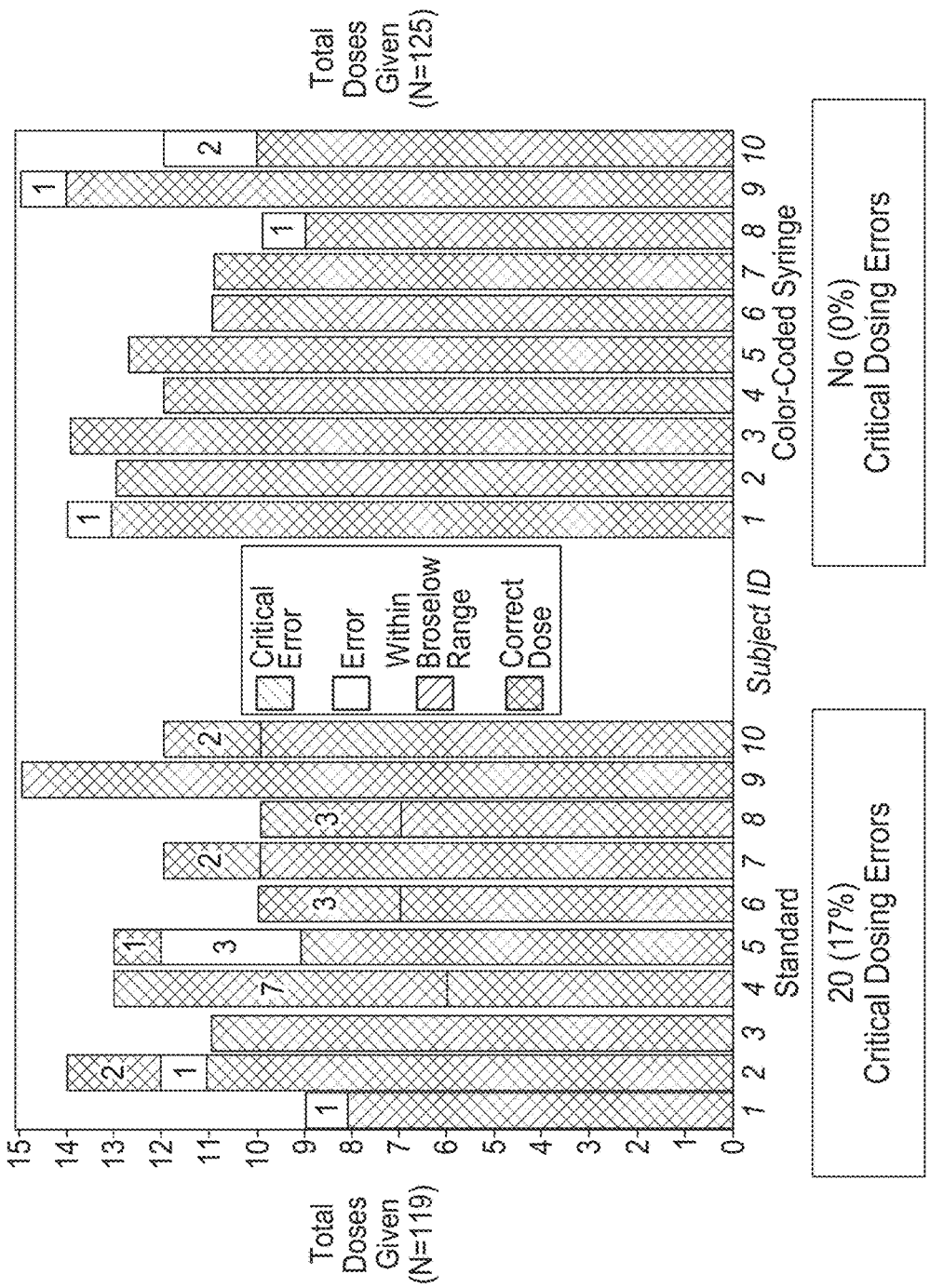
FIGS. 8A-8F includes data showing improvements in the drug delivery using the system and methods of the current disclosure.
Figure 8B:
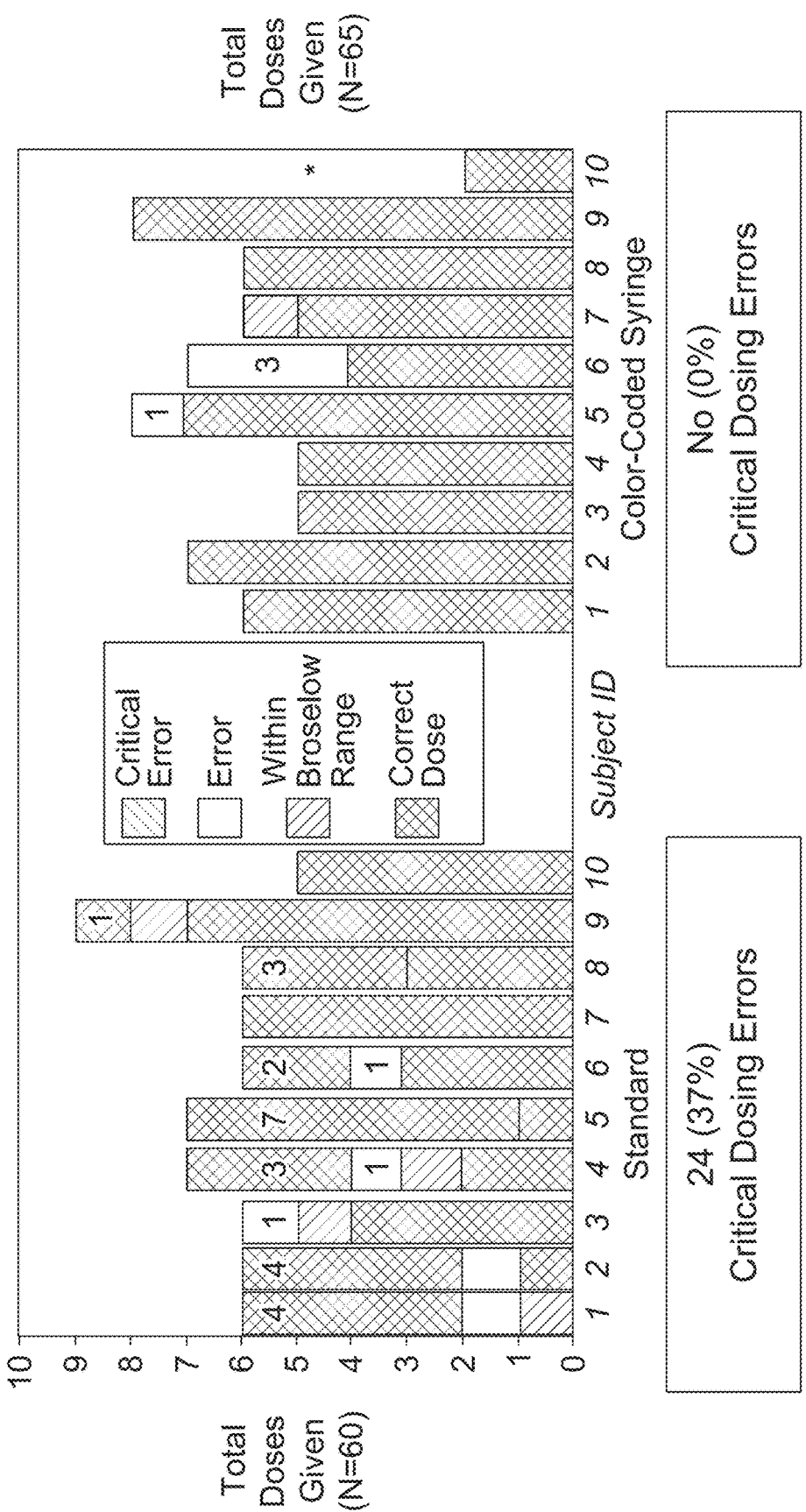
Figure 8C:
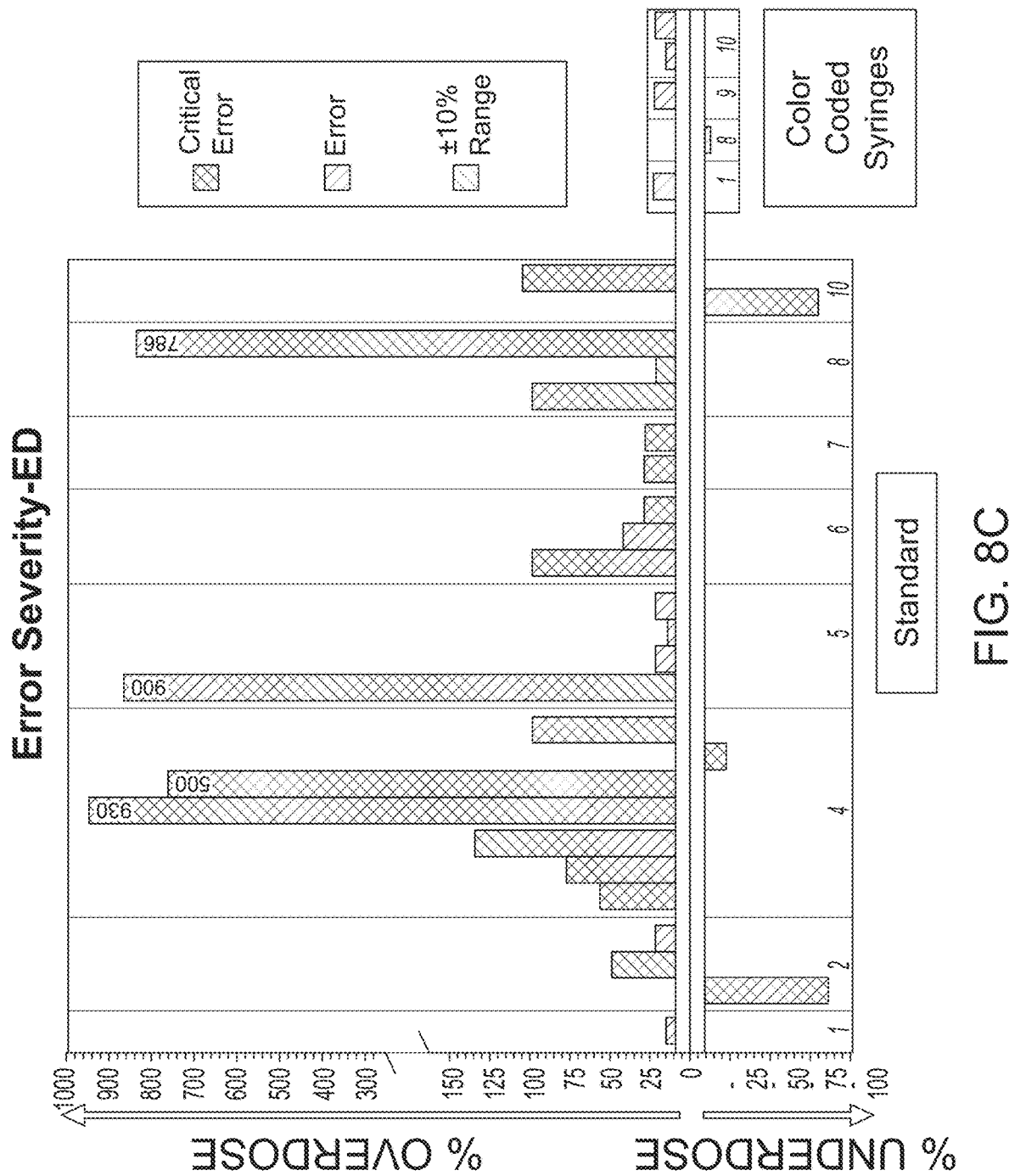
Figure 8D:
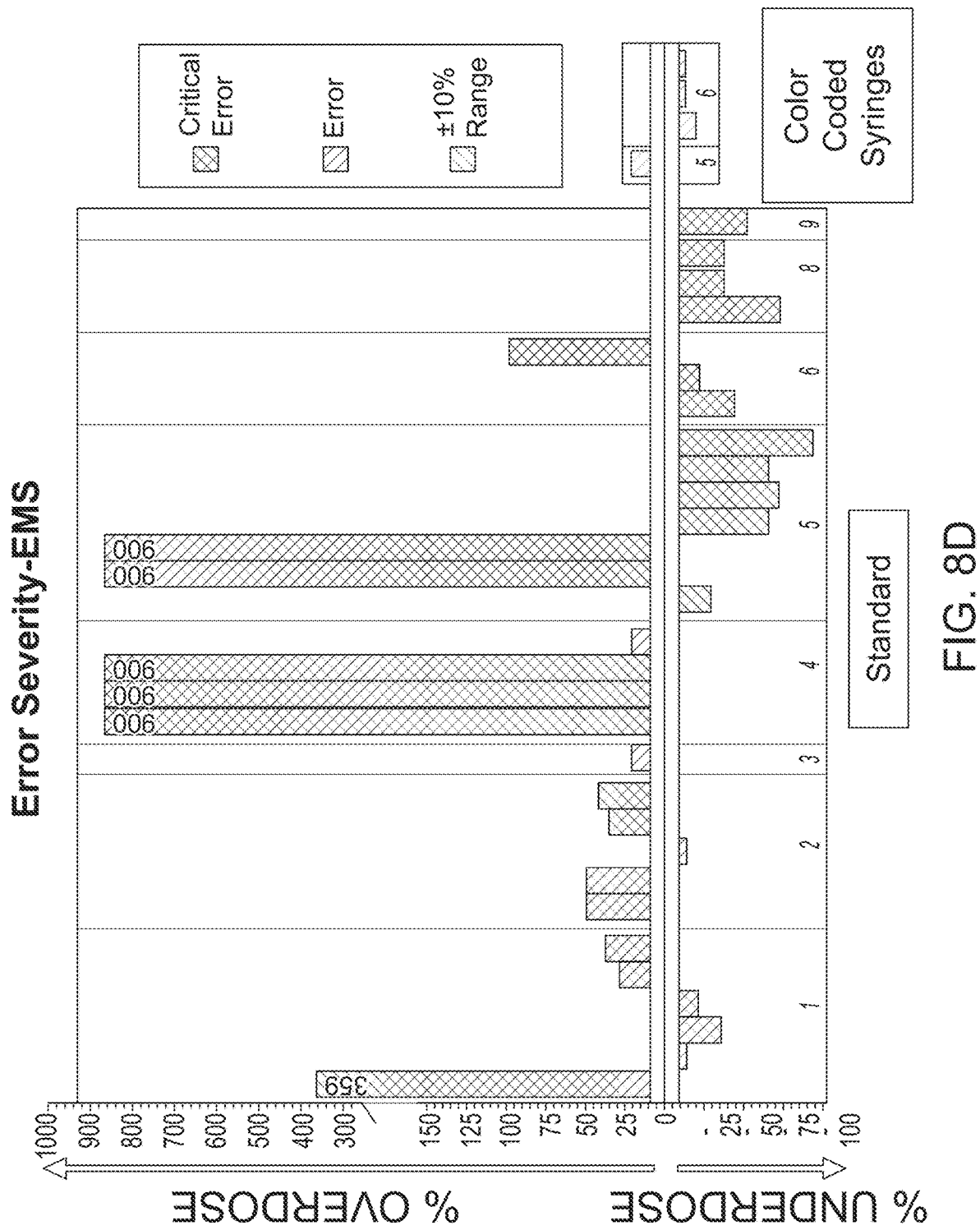
Figure 8E:
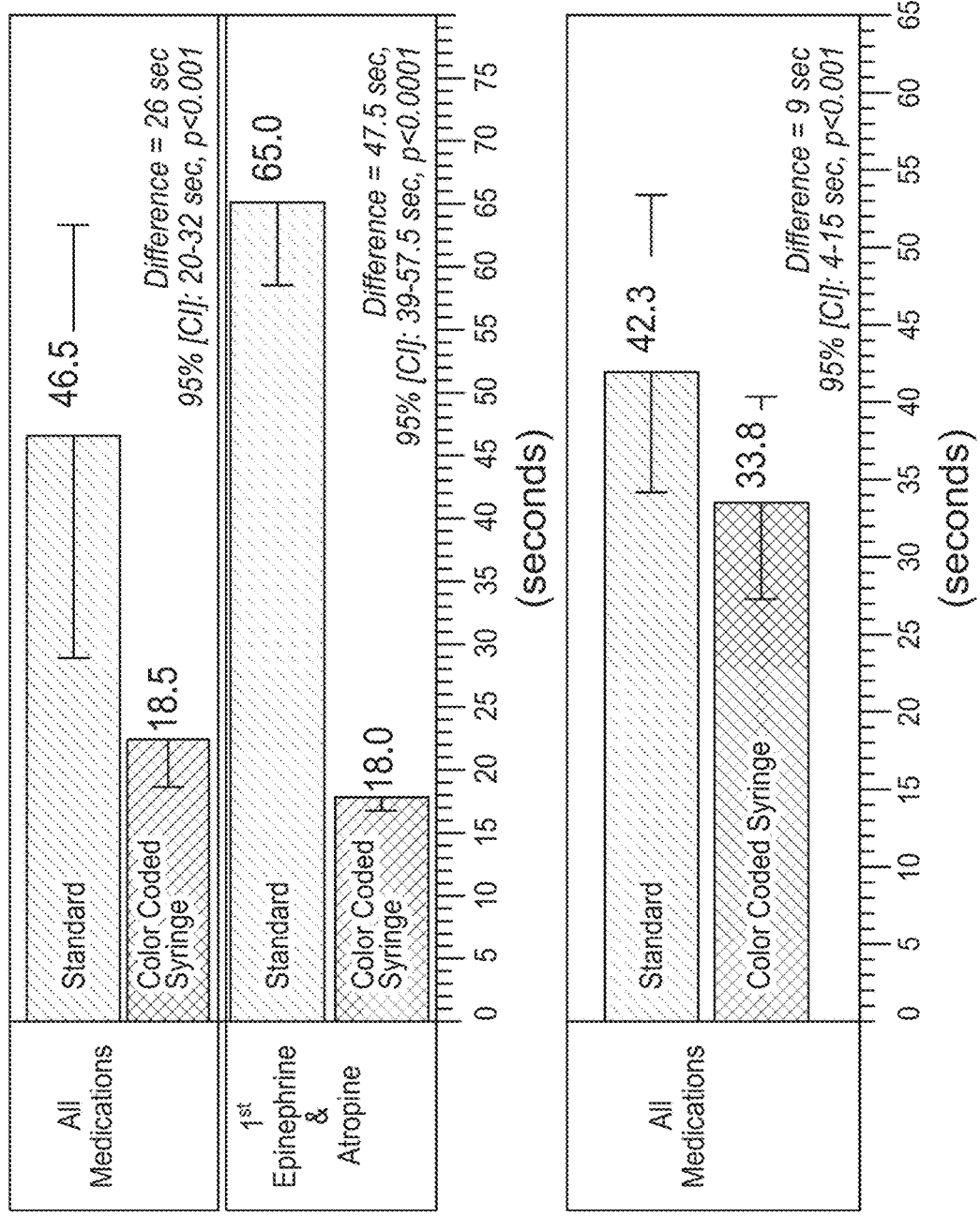
Figure 8F:
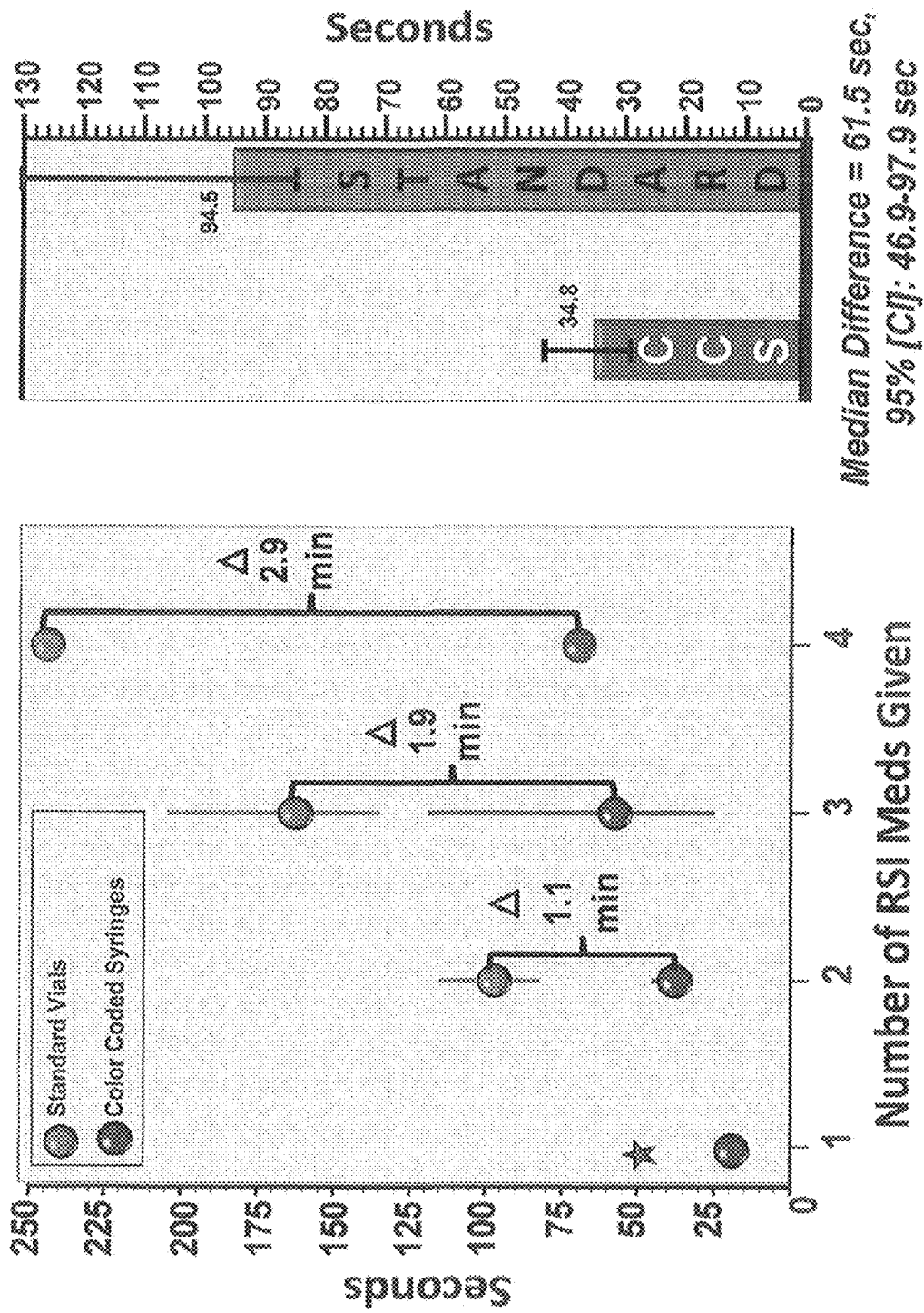

Thus, as disclosed with reference to all the figures, the pre-labeled medicine dispensing device and the method of making and using it offers several advantages over the currently used systems and methods. First, the pre-marked medicine dispensing device allows to administer medication more accurately as compared to any of the currently available systems. Furthermore, as shown in FIGS. 8A and 8B, eliminating the step of calculating dosages that need to be administered in the high stress environment, as well as eliminating the steps of selecting appropriate medicine dosing device helps to eliminate critical dosing errors, such as critical over dose or critical under dose errors, that usually arise when conventional devices and methods are used. Also, frequency and severity of non-critical errors as compared to the traditional methods can be reduced as shown in FIGS. 8C and 8D. Lastly, as shown in FIGS. 8E and 8F, time to prepare and deliver medication, as well as time to deliver medications when preparing for rapid sequence intubations (RSI) may be significantly reduced when the medicine-dosing device according to the current disclosure is used as compared to the conventional devices. As such the pre-labeled medicine dispensing device designed and used in accordance with the disclosed embodiments provides for more simplified, accurate and efficient drug delivery in emergency and critical care situations.

I claim:

1. A method of generating a customized dosing label sized for a medicine dispensing device of a particular size, comprising:
    selecting a drug to be administered;
    printing a plurality of color coded zones of varying widths upon the dosing label on a medium separate from but configured to be fixedly attached to the medicine dispensing device; wherein volume markings are within each of the color coded zones and the varying widths of the plurality of color coded zones are determined by:
    determining appropriate drug doses that correspond to one or more physical characteristics of a patient,
    determining a concentration of a drug solution containing the drug to be administered;
    determining a volumetric capacity of the medicine dispensing device based on a length and a width of the medicine dispensing device; and
    calculating, using a conversion factor based upon the volumetric capacity, a width for each individual color coded zone of the plurality of color coded zones that represent the appropriate drug doses that correspond to the one or more physical characteristics of the patient;
    applying at least one alignment mark to the generated dosing label, the at least one alignment mark configured to ensure alignment of the generated dosing label when the generated dosing label is fixedly attached to the medicine dispensing device; and
    wherein the drug solution, when filled within the medicine dispensing device can be seen through the plurality of color coded zones on the dosing label.

2. The method of claim 1, wherein the volumetric capacity of the medicine dispensing device is printed on the dosing label.

3. The method of claim 1, wherein the plurality of color coded zones are translucent.

4. The method of claim 3, wherein the medicine dispensing device is a syringe, and further comprising affixing the generated dosing label to an exterior surface of the syringe.

5. The method of claim 4, wherein the generated dosing label is affixed to the exterior surface of the syringe such that the width of each individual color coded zone extends around a circumference of the syringe.

6. The method of claim 5, wherein a first end of a color coded zone corresponds to a first line around at least a portion of the circumference of the syringe, and a second end of the color coded zone corresponds to a second line around at least a portion of the circumference of the syringe, such that each edge of each color coded zone is marked by a line around at least a portion of the circumference of the syringe.

7. The method of claim 3, further comprising adjusting a size of the generated dosing label depending at least in part on the volumetric capacity of the medicine dispensing device.

8. The method of claim 7, wherein the size of the generated dosing label is configured such that the generated dosing label covers an outer surface of the medicine dispensing device.

9. The method of claim 7, wherein the generated dosing label is fixedly attached such that the generated dosing label covers an outer surface on the medicine dispensing device.

10. The method of claim 3, wherein the at least one alignment mark indicates a direction for the generated dosing label to be fixedly attached to the medicine dispensing device.

11. The method of claim 10, wherein the generated dosing label further comprises the concentration of the drug solution containing the drug.

12. The method of claim 3, wherein the generated dosing label further comprises a name of the drug to be administered.

13. The method of claim 1, wherein the plurality of color coded zones on the dosing label are configured to allow verification of a correct dose for the patient.

14. A method of generating a dosing label sized for a medicine dispensing device, comprising:
   printing a plurality of color coded zones of varying widths upon the dosing label separate from but configured to be affixed to the medicine dispensing device; wherein volume markings are within each of the color coded zones and the varying widths of the plurality of color coded zones are determined by:
   determining appropriate drug doses of a drug that correspond to at least one physical characteristic of a patient, wherein the determining the appropriate drug doses further comprises:
      determining a concentration of the drug in a drug solution;
      selecting the medicine dispensing device to which the dosing label is to be affixed, the medicine dispensing device being of a volumetric capacity; and
      calculating, by a computer processing unit, a width for each individual color coded zone of the plurality of color coded zones,
   wherein the calculating is based on
      the concentration of the drug in the drug solution,
      the volumetric capacity of the medicine dispensing device, and
      a unique conversion factor based on the volumetric capacity;
   with at least one of the individual color coded zones of the plurality of color coded zones having a width that is different from at least a second one of the individual color coded zones of the plurality of color coded zones, with each individual color coded zone of the plurality of color coded zones corresponding to a drug dose that is based on one of the at least one physical characteristic of the patient; and
   wherein the drug solution, when filled within the medicine dispensing device, can be seen through the plurality of color coded zones on the dosing label.

15. The method of claim 14 wherein the volumetric capacity of the medicine dispensing device is printed on the dosing label.

16. The method of claim 15 wherein the concentration of the drug in the drug solution is also printed on the dosing label.

17. The method of claim 14 wherein the plurality of color coded zones included on the dosing label serve as a reminder of a correct volume of the drug to be given to the patient.

18. The method of claim 14, further comprising applying at least one alignment mark to the dosing label, the at least one alignment mark indicating a direction for the dosing label to be affixed to the medicine dispensing device.

19. The method of claim 18 wherein the at least one alignment mark is placed at an edge of the dosing label to be aligned with a distal end of the medicine dispensing device.

20. The method of claim 18 wherein the at least one alignment mark is placed in one of the plurality of color coded zones included on the dosing label.

21. The method of claim 14, wherein the plurality of color coded zones included on the dosing label are translucent.

22. The method of claim 14, wherein each of the plurality of color coded zones has the width defined by leading and trailing edges parallel to opposing ends of the dosing label and wherein solid black lines are included at boundaries between ones of the plurality of color coded zones.

* * * * *